United States Patent
Kinghorn et al.

(10) Patent No.: US 6,737,439 B2
(45) Date of Patent: May 18, 2004

(54) **AROMATASE INHIBITORS FROM *BROUSSONETIA PAPYRIFERA***

(75) Inventors: Alan Douglas Kinghorn, Chicago, IL (US); John M. Pezzuto, River Forest, IL (US); Dongho Lee, Chicago, IL (US); Krishna P. L. Bhat, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 10/205,029

(22) Filed: Jul. 25, 2002

(65) Prior Publication Data

US 2003/0125377 A1 Jul. 3, 2003

Related U.S. Application Data

(60) Provisional application No. 60/310,643, filed on Aug. 7, 2001.

(51) Int. Cl.$^7$ .................. A61K 31/35; C07D 493/00
(52) U.S. Cl. .................. 514/455; 514/456; 514/457; 549/387; 549/400; 549/401
(58) Field of Search ............... 549/387, 400, 549/401; 514/455, 456, 457

(56) References Cited

PUBLICATIONS

C.L. Vogel, *Semin. Oncol.*, 23, (Suppl. 9), pp. 2–9 (1996).
P. Reddy, *J. Clin. Pharmacol. Ther.*, 23, pp. 81–90 (1998).
D. Henderson et al., *Steroids*, 50, pp. 219–233 (1987).
J.P. Karr et al., *Steroids*, 50, pp. 441–449 (1987).
G.J. Kelloff et al., *Cancer Epidemiol. Biomark. Prev.*, 7, pp. 65–78 (1998).
P.K. Siiteri, *Cancer Res.* 42, (Suppl. 8), pp. 3269s–3273s (1982).
A.M.H. Brodie et al., *Semin. Oncol.*, 23 (Suppl. 9), pp. 10–20 (1996).
Chiang Su New Medicinal College, Ed., Dictionary of Chinese Crude Drugs, Shanghai Scientific Technologic Publisher, Shanghai, pp. 2289–2290 (1986).
H. Matsuda et al., *Biol. Pharm. Bull.*, 18, pp. 463–466 (1995).
S.Y. Kim et al. *J. Am. Oil Chem. Soc.*, 71, pp. 633–640 (1994).
S.Y. Kim et al., *Kor. J. Pharmacogn.*, 25, pp. 388–394 (1994).
A. Shirata et al., *Sanshi Shikenjo Kokoku*, 28, pp. 691–705 (1982).
H.–H. Ko et al., *J. Nat. Prod.*, 60, pp. 1008–1011 (1997).
C.–N. Lin et al., *J. Nat. Prod.*, 59, pp. 834–838 (1996).
S.–C. Fang et al., *Phytochemistry*, 37, pp. 851–853 (1994).
S.–C. Fang et al., *Phytochemsitry*, 38, pp. 535–537 (1995).
M. Takasugi et al., *Chem. Lett.*, pp. 339–340 (1980).
M. Takasugi et al., *Chem. Lett.*, pp. 1459–1460 (1980).
M. Takasugi et al., *Chem. Lett.*, pp. 689–692 (1984).

M. Takasugi et al., *Chem. Lett.*, pp. 693–694 (1984).
J. Matsumoto et al., *Chem. Pharm. Bull*, 33, pp. 3250–3256 (1985).
J. Ikuta et al., *Heterocycles*, 23, pp. 2835–2842 (1985).
T. Fukai et al., *Chem. Pharm. Bull.*, 34, pp. 1987–1993 (1986).
H.–J. Jeong et al., *Arch. Pharmacal Res.*, 22, pp. 309–312 (1999).
J.C. LeBail et al., *Cancer Lett.*, 133, pp. 101–106 (1998).
F. Ferrari et al., *Planta Med.*, 55, pp. 70–72 (1989).
G. Cardillo et al., *J. Chem. Co*, (C), pp. 3967–3970 (1971).
M.–I Chung et al., *J. Nat. Prod*, 62, pp. 1033–1035 (1999).
M.–I. Chung et al., *Phytochemistry*, 44, pp. 943–947 (1997).
I.S. Mann et al., *Tetrahedron*, 47, pp. 7991–8000 (1991).
v. Roussis et al., *Phytochemistry*, 26, pp. 2371–2375 (1987).
W. Gaffield, *Tetrahedron*, 26, pp. 4093–4108 (1970).
T. Hanato et al., *Chem. Pharm. Bull.*, 36, pp. 2090–2097 (1988).
V.S. Kamat et al., *Heterocycles*, 15, pp. 1163–1170 (1981).
C.–H. Chang, *Phytochemistry*, 40, pp. 945–947 (1995).
M. Mizuno et al.,*Phytochemistry*, 29, pp. 2738–2740 (1990).
D.A.D. Barros et al., *Phytochemistry*, 21, pp. 2107–2109 (1982).
G. delle Monache et al., *Phytochemistry*, 39, pp. 575–580 (1995).
S. Matsuyama et al., *Agric. Biol. Chem.*, 55, pp. 1333–1341 (1991).
A.V. Rama Rao et al., *Tetrahedron Lett.*, 24, pp. 3013–3016 (1983).
K. Doi et al., *Chem. Pharm. Bull.*, 49, pp. 151–153 (2001).
J. Li et al., *Phytochemistry*, 28, pp. 3564–3566 (1989).
V.K. Bhalla et al., *Tetrahedron Lett.*, 20, pp. 2401–2406 (1968).
J. Reisch et al., *Phytochemistry*, 23, pp. 2114–2115 (1984).
T. Fukai et al., *Heterocycles*, 31, pp. 373–382 (1990).
N.N. Gerber, *Phytochemistry*, 25, pp. 1697–1699 (1986).
L. Pistelli et al., *Phytochemistry*, 42, pp. 1455–1458 (1996).
M. Takasugi et al., *Chem. Lett.*, pp. 1239–1240 (1978).
I. Fernandez et al., *Phytochemistry*, 34, pp. 733–736 (1993).
E. Mannila et al., *Phytochemistry*, 33, pp. 813–816 (1993).
K. Hirakura et al., *Heterocycles*, 23, pp. 2239–2242 (1985).
J.T. Kellis et al., *Science*, 225, pp. 1032–1034 (1984).
A.–R. Ibrahim et al., *J. Steroid Biochem. Molec. Biol.*, 37, pp. 257–260 (1990).

(List continued on next page.)

*Primary Examiner*—D. Margaret Seaman
*Assistant Examiner*—Raymond Covington
(74) *Attorney, Agent, or Firm*—Marshall, Gerstein & Borun LLP

(57) ABSTRACT

A composition and method of cancer treatment is disclosed. The composition and method utilized the extract of *B. papyrifera*, or compounds included therein having aromatase inhibition properties, as active cancer chemopreventative and treating agents in mammals, including humans.

18 Claims, No Drawings

PUBLICATIONS

E.A. Thompson et al., *J. Biol. Chem., 249*, pp. 5373–5378 (1974).

T. Rabe et al., *J. Steroid Biochem. 17*, pp. 305–309 (1982).

D. Lee et al., *J. Nat. Prod., 64*, 1286–1293 (2001).

Y. Kao et al., *Environmental Health Perspectives, 106*, No. 2, 85–92 (1998).

J. LeBail et al., *Life Sciences, 68*, 751–761 (2001).

L.M. Knowles et al., *Nutrition and Cancer, 38*(1), 116–122 (2000).

F.V. So et al., *Cancer Letters, 112*, 127–133 (1997).

N. Guthrie et al., Abstracts of Papers American Chemical Society, 219, No. 1–2, p. AGFD 183 (2000).

P. J. Harrison et al., *FASEB Journal, 15*, No. 4, p. A630 (2001).

T. Hatano et al., *Chem. Pharm. Bull., 36*(6), 2286–2288 (1988).

K. Miyamoto et al., *Chemistry Abstracts*, JP 2304024 (1990).

A. Yoshihiso et al., *Phytochemistry, 47*, No. 3, 389–392 (1998).

I. Lee, *Chemical Abstracts*, STN Database accession No. 121:246195 (1994).

T. Yanagisawa et al., *Chemical Abstracts*, JP 3068518 (1991).

J. Zeng et al., *Chemical Abstracts*, STN Database accession No. 132:291004 (1999).

R.C. Ronald et al., *Journal of Organic Chemistry, 49*(9), 1658–60 (1984).

AROMATASE INHIBITORS FROM *BROUSSONETIA PAPYRIFERA*

CROSS REFERENCE TO RELATED APPLICATIONS

This application claims the benefit of U.S. provisional application Serial No. 60/310,643, filed Aug. 7, 2001.

STATEMENT OF GOVERNMENTAL INTEREST

This invention was made with governmental support under Grant No. POI CA48112 awarded to NCI, National Institutes of Health, Bethesda, Md.

FIELD OF THE INVENTION

The present invention relates to compounds and compositions that are potent and selective inhibitors of the aromatase enzyme system, and in particular, to aromatase inhibitors extracted from *Broussonetia papyrifera*. The present invention also relates to cancer chemopreventive compositions and methods. More particularly, the present invention relates to cancer chemoprevention in mammals, including humans. The present invention further relates to methods of treating conditions and diseases wherein inhibition of aromatase provides a benefit, such as breast cancer, prostate cancer, and other hormone-dependent cancers.

BACKGROUND OF THE INVENTION

Chemoprevention, i.e., the prevention of cancer by administration of chemical agents that reduce the risk of carcinogenesis is one of the most direct ways to reduce cancer-related morbidity and mortality. See, M. B. Sporn, *Fed. Proc.*, 38, p. 2528 (1979). However, chemoprevention requires the identification of carcinogens and chemopreventatives, even though interactions between the factors that modulate cancer risk are complex. Whereas extensive efforts have been made to identify carcinogens and mutagens, the identification of chemopreventative agents has received less attention.

Cancer chemopreventive agents include nonsteroidal antiinflammatory drugs (NSAIDs), such as indomethacin, aspirin, piroxicam, and sulindac, all of which inhibit cyclooxygenase. There is a need in the art, however, for the identification of additional specific compounds that have a cancer chemopreventative effect on mammals. To this end, investigators have searched for new cancer chemopreventative agents by evaluating hundreds of plant extracts for a potentially active compounds. Such cancer chemopreventative compounds then can be used in drug compositions to reduce the risk of, or to treat, a cancer, such as breast or prostate cancer, and other hormone-dependent cancers.

Breast cancer is a major cause of morbidity and mortality in women throughout the world. Epidemiological and experimental evidence strongly support a role for estrogens in the development and growth of breast cancer. A role for estrogens in prostate neoplasia has also been postulated. Therefore, one chemotherapeutic or chemopreventive strategy for breast cancer and prostate cancer control is to decrease estrogen production.

An alternative approach to the endocrine treatment of estrogen-dependent breast cancer is the reduction of the supply of estrogens to the tumor. In the treatment of hormone-dependent breast cancer, estrogen receptors can be blocked with antagonists, such as tamoxifen. Gonadotrophin can be inhibited by a continuous administration of gonadatrophin-releasing hormone (GnRH) or one of its analogues. P. M. Conn et al., *N. Engl. J. Med.*, 324, pp. 93–103 (1991). Estrogens are biosynthesized from androgens by a microsomal cytochrome P450 enzyme complex system termed aromatase. P. K. Siiteri, *Cancer Res.*, 42, (Suppl. 8), pp. 3269s–3273s (1982).

Accordingly, the inhibition of aromatase, an enzyme that catalyzes the final, rate-limiting step in estrogen biosynthesis, is an effective approach in the treatment of breast and prostate cancers. The use of aromatase inhibitors is of clinical interest for cancer therapy, and selective and potent aromatase inhibitors have been developed.

Recent studies on the fundamental biologic properties of the very complex aromatase enzyme system yielded information concerning genetic control, differential tissue expression, and modulation by a variety of growth factors and cytokines present within the tumor environment. H. A. Harvey, *Semin. Oncol.*, 23 (Suppl. 9), pp. 33–38 (1996). Using monoclonal or polyclonal antibodies against aromatase, it has been demonstrated that a significant amount of aromatase accumulates in breast tumors and the stroma surrounding breast tumors. R. J. Santen et al., *Endocr. Rev.*, 11, 221–265 (1994). This finding may be of relevance in the initiation of breast carcinoma, and in the development of compounds of sufficient potency to effectively lower plasma levels of estrogen by inhibiting estrogen synthesis in situ. Because estrogen production is the last step in the biosynthetic sequence of steroid production, selective inhibition of aromatase would not interfere with the production of other steroids, such as adrenal corticoids. For these reasons, aromatase is a particularly attractive enzyme target for selective inhibition in the treatment of cancers.

Several classes of aromatase inhibitors, such as substrate androstenedione derivatives, the nonsteroidal aminoglutethimide and its analogues, imidazoles, and triazoles, have been developed over the past twenty years as potential therapeutic agents. G. J. Kelloff et al., *Cancer Epidemiol. Biomark. Prev.*, 7, pp. 65–78 (1998). Aminoglutethimide (AG) was the first aromatase inhibitor used clinically. AG effectively reduces N-methyl-N-nitrosourea (MNU)-induced tumor incidence in Sprague-Dawley rats when administered at 400 mg/kg diet. However, the nonselectivity of this compound to aromatase, its structural similarity to phenobarbital and the associated CNS effects, and lack of potency compared to the triazole aromatase inhibitors has led to its decreasing use. Rogletimide, an AG analogue, is a more specific, but less potent aromatase inhibitor than AG, and also is effective in reducing the testosterone-induced increase in tumor size.

Several other triazole, nonsteroidal aromatase inhibitors are effective aromatase inhibitors. For example, vorozole is one of the most potent and specific aromatase inhibitors, in vitro and in vivo. At p.o. (per os, or oral) doses of 5 mg/kg, vorozole decreases the % tumor incidence from 100 to 10, and the tumor multiplicity from 5 to 0.1 tumors/animal, in Sprague-Dawley rats. However, one major disadvantage of vorozole is that it has a weak androgenic activity and, as a result, the treated animals appeared bulky and heavily muscled. Among the steroidal inhibitors, exemustane (administered subcutaneously) was effective in causing tumor regression and preventing the formation of new tumors. Exemustane, however, has androgenic effects similar to vorozole.

The present invention is directed to potent and selective aromatase inhibitors that do not exhibit the disadvantages and drawbacks associated with prior aromatase inhibitors.

SUMMARY OF THE INVENTION

In a programmed research effort to discover novel, natural product-based cancer chemopreventive agents, i.e., agents capable of preventing, inhibiting, or reversing the process of carcinogenesis, about four thousand plant samples from around the world were extracted with an organic solvent, and the dried extracts so produced were tested in an array of bioassays reflective of modulating carcinogenesis at the stage of initiation, promotion, or progression. As a result of this research, an ethyl acetate-soluble extract of a domestic plant called *Broussonetia papyrifera* was found to exhibit a potent aromatase inhibitory activity.

*Broussonetia papyrifera* is a deciduous tree that is naturalized in the United States, parts of which have been used for treatment of impotency and ophthalmic disorders in the People's Republic of China. In a search for edible aromatase inhibitors, an extract of *B. papyrifera* was found to have significant activity (0.4 µg/ml). Extracts of *B. papyrifera* have shown antifungal, antihepatotoxic, antioxidant, and aldose reductase inhibitory activities. Also, several flavonoid constituents of this plant have been shown to inhibit lipid peroxidation and to exhibit antiplatelet effects.

Bioassay-guided fractionation of a *Broussonetia papyrifera* extract using an in vitro aromatase inhibition assay led to the isolation of both novel and known active compounds. The compounds included coumarins, benzofurans, biphenylpropanes, and various types of flavonoids.

Flavonoids are natural components which are present in many plants known to be constituents of animal and human diet. These compounds exhibit a variety of biological properties, such as antiviral, antiinflamatory, antimutagenic, and anticarcinogenic activities. J. D. LeBail et al., *Cancer Lett.*, 133, pp. 101–106 (1998). Studies have shown that some flavones, isoflavones, and flavanones alter hormone production and inhibit aromatase activity in human and ovarian microsomes. In addition, due to their structural similarity to estrogens, some flavonoids bind to the estrogen receptor and possess mixed agonist/antagonist properties. B. M. Collins et al., *Steroids*, 62, pp. 365–372 (1997).

Based on this observation, purification of the constituents of the plant extract responsible for the biological activity was traced using an in vitro aromatase inhibition assay, and identified using spectroscopic techniques to a first flavonoid of novel structure, (2S)-2',4'-dihydroxy-2"-(1-hydroxy-1-methylethyl)-dihydrofuro[2,3-h]flavanone (11), and a second flavonoid of previously known structure, isolicoflavonol (i.e., 3,5,7,4'-tetrahydroxy-3'-prenylflavone) (12).

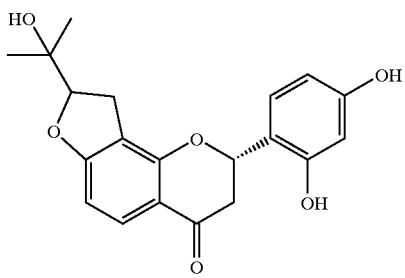

11

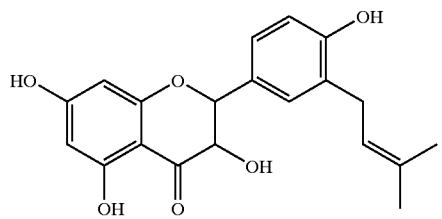

12

Compounds 11 and 12 (at about 0.1 µM) exhibited an approximately 60-fold greater potency for aromatase inhibitors compared to aminoglutethimide (AG), the positive control used for this assay. Initially, some of the compounds isolated from *B. papyrifera* were tested for binding to the estrogen receptor-α or -β. J. A. Gustafsson, *J. Endocrinol.*, 163, pp. 379–383 (1999). Interestingly, none of the aromatase active compounds showed significant binding to either of the receptors. Also, the effectiveness of some of the flavonoids against the inhibition of quinone reductase, a phase II enzyme involved in detoxification mechanisms, was evaluated. L. C. Chang et al., *J. Nat. Prod.*, 60, pp. 869–873 (1997); and P. Talalay, *Proc. Natl. Acad. Sci. USA*, 85, pp. 8261–8265 (1998). No significant inhibition of aromatase was observed by any of the agents tested. Compound 11 also was effective in inhibiting (50%) the formation of alveolar lesions in a mouse mammary organ culture model when tested at 100 ng/ml. R. G. Mehta et al., *Anticancer Res.*, 14, pp. 1209–1213 (1994).

The present invention, therefore, is directed to the chemotherapy or chemoprevention of estrogen-dependent breast and prostate cancers. While even more potent aromatase inhibitors have been developed, the compounds isolated from *B. papyrifera* demonstrated a very potent inhibition of aromatase, and are isolated from a common, natural, and renewable source. Also, the compounds from *B. papyrifera* are based on nonsteroidal moieties, unlike any current class of inhibitors, and are natural products that have reduced toxicity and, therefore, a wider acceptance in the general population.

The present invention, therefore, is directed to cancer chemopreventative agents, compositions containing the agents, and methods of using the chemopreventative agents to prevent and/or treat a cancer, like breast cancer or prostate cancer. In particular, the present invention is directed to compositions containing one or more compounds found in an extract from *Broussonetia papyrifera* and that are capable of inhibiting the aromatase enzyme system, and use of the compositions in methods of cancer chemoprevention.

An important aspect of the present invention, therefore, is to provide a method and composition for preventing or treating a cancer using one or more compounds found in an extract from *Broussonetia papyrifera* and capable of inhibiting the aromatase enzyme system.

Another aspect of the present invention is to overcome the problem of high mammalian toxicity associated with present cancer chemopreventative agents by using a natural product-derived compound.

Still another aspect of the present invention is to overcome the problem of insufficient availability associated with synthetic anticancer agents by utilizing readily available, and naturally occurring, chemopreventative agent.

Another important aspect of the present invention is to provide a drug composition containing one or more compounds found in an extract from *Broussonetia papyrifera* and capable of inhibiting the aromatase enzyme system, and that can be administered to chemoprevent cancers.

These and other aspects of the present invention will become apparent from the following detailed description of the preferred embodiments of the invention.

DETAILED DESCRIPTION OF THE PREFERRED EMBODIMENTS

The present invention provides compounds and compositions that selectively inhibit aromatase activity and are present in the extract of *B. papyrifera*. The invention further provides methods of inhibiting aromatase activity, including methods of selectively inhibiting the activity of aromatase. The methods include in vitro, in vivo, and ex vivo applications.

Of particular benefit are methods of selectively inhibiting aromatase activity in the clinical setting in order to ameliorate diseases or disorders mediated by aromatase activity. Thus, treatment of diseases or disorders characterized by excessive or inappropriate aromatase activity can be treated through use of selective inhibitors of aromatase present in the extract of *B. papyrifera*.

Moreover, the invention provides pharmaceutical compositions comprising the extract of *B. papyrifera* or selective aromatase inhibitors found in the extract of *B. papyrifera*. Also provided are articles of manufacture comprising a selective aromatase inhibitor compound found in the extract of *B. papyrifera* (or a pharmaceutical composition comprising the compound) and instructions for using the compound.

The methods described herein benefit from the use of compounds found in the extract of *B. papyrifera* that selectively inhibit, and preferably specifically inhibit, aromatase activity in vitro, in vivo, or ex vivo. Of particular advantage, the inhibition can be in vivo, i.e., in a living subject, e.g., an animal or human, wherein an aromatase inhibitor can be used as a therapeutic to inhibit aromatase activity in the subject.

The term "selective aromatase inhibitor" as used herein refers to a compound that inhibits aromatase more effectively than other enzymes. A "selective aromatase inhibitor" compound is understood to be more selective for aromatase than compounds conventionally and generically designated aromatase inhibitors, e.g., aminoglutethimide. Concomitantly, aminoglutethimide is deemed a "nonselective aromatase inhibitor."

The relative efficacies of compounds used as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration of "$IC_{50}$." $IC_{50}$ determinations can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, or other inhibitory concentration.

Accordingly, a "selective aromatase inhibitor" alternatively can be understood to refer to a compound that exhibits a 50% inhibitory concentration ($IC_{50}$) with respect to aromatase that is at least 10-fold, preferably at least 20-fold, and more preferably at least 30-fold, lower than the $IC_{50}$ value with respect to any or all of the other related enzymes. The term "other related enzymes" means other cytochrome P450 enzymes, estrone sulfates, and enzymes involved in androgen or estrone biosynthesis or metabolism, and the like. The term "specific aromatase inhibitor" can be understood to refer to an aromatase inhibitor compound that exhibits an $IC_{50}$ with respect to aromatase that is at least 50-fold, preferably at least 100-fold, more preferably at least 200-fold, and still more preferably at least 500-fold, lower than the $IC_{50}$ with respect to any or all of the other related enzyme family members.

For the purposes of the description herein, the term "treatment" includes preventing, lowering, stopping, or reversing the progression of severity of the condition or symptoms being treated. As such, the term "treatment" includes both medical therapeutic and/or prophylactic administration, as appropriate.

Bioassay-guided fractionation of an ethyl acetate-soluble extract from the whole plants of *Broussonetia papyrifera*, a naturalized plant in the United States, using an in vitro aromatase inhibition assay, led to the isolation of five novel active compounds, 5,7,2',4'-tetrahydroxy-3-geranylflavone (1), isogemichalcone C (8), 3'-[γ-hydroxymethyl-(E)-γ-methylallyl]-2,4,2',4'-tetrahydroxychalcone 11'-O-coumarate (9), demethylmoracin I (10), and (2S)-2',4'-dihydroxy-2"-(1-hydroxy-1-methylethyl)-dihydrofuro[2,3-h]flavanone (11), and ten known (12–21) compounds, which were also found to be active. Of these compounds, the most potent inhibitors were compounds 9 ($IC_{50}$ 0.5 μM), 11 ($IC_{50}$ 0.1 μM), isolicoflavonol (12, $IC_{50}$ 0.1 μM), and (2S) abyssinone II (13, $IC_{50}$ 0.4 μM).

Additionally, six novel compounds, 5,7,3',4'-tetrahydroxy-6-geranylflavonol (2), 5,7,3',4'-tetrahydroxy-3-methoxy-6-geranylflavone (3), (2S)-7,4'-dihydroxy-3'-prenylflavan (4), 1-(2,4-dihydroxyphenyl)-3-(4-hydroxyphenyl)propane (5), 1-(2,4-dihydroxy-3-prenylphenyl)-3-(4-hydroxyphenyl)propane (6), and 1-(4-hydroxy-2-methoxyphenyl) -3-(4-hydroxy-3-prenylphenyl) propane (7), were isolated and characterized, but proved to be inactive as aromatase inhibitors, as were an additional twenty-one known compounds.

The structures of the novel compounds 1–11 were elucidated by spectroscopic methods. Structure-activity relationships in the aromatase assay were determined for the benzofurans, biphenylpropanoids, coumarins, and various types of flavonoids (chalcones, flavans, flavanones, and flavones) obtained among a total of forty-two extracted constituents of *B. papyrifera*.

Epidemiological and experimental evidence strongly support a role for estrogens in the development and growth of breast cancer.[1,2] Similarly, the participation of estrogens in prostate neoplasia has been postulated.[3,4] Therefore, one chemotherapeutic or chemopreventive strategy for breast and prostate cancer control is to decrease estrogen production.[5] Accordingly, inhibition of aromatase, an enzyme that catalyzes the final, rate-limiting step in estrogen biosynthesis,[6] is being explored as a target germane to the treatment or prevention of breast and prostate cancers.[5] Aminoglutethimide and its analogues can be considered prototype aromatase inhibitors, and based on the same mechanism of action, substrate androstenedione derivatives, imidazoles, and triazoles have been developed over the past 20 years. [5,7]

*Broussonetia papyrifera* (L.) L'Hér. ex Vent. (Moraceae) is a deciduous tree, and its fruits have been used for impotency and to treat ophthalmic disorders. [8,9] Extracts of *B. papyrifera* have shown antifungal, [10] antihepatotoxic, [11] antioxidant, [12] and lens aldose reductase inhibitory activities. [9] Also, several flavonoid constituents of this plant have been shown to inhibit lipid peroxidation[13] and to exhibit antiplatelet effects.[14] Previous phytochemical work on this plant has resulted in the isolation of coumarins,[15] triterpenoids,[16] and various types of flavonoids.[15,17–24]

As part of a search for cancer chemopreventive agents of natural origin, an ethyl acetatesoluble extract of *B. papyrifera* was found to significantly inhibit aromatase activity in an in vitro assay (74% inhibition at 80 µg/mL). Bioassay-guided fractionation of the ethyl acetate-soluble extract of *B. papyrifera* using this assay led to the isolation of five novel (1, 8–11) and ten known 12–21) compounds that were found to be active. Additionally, six novel compounds (2–7) and twenty-one known compounds were isolated and characterized as inactive when evaluated with this in vitro aromatase assay.[25,26] Isolation and identification of active and/or novel compounds were accomplished using the aromatase inhibition assay to guide chromatographic purification.

From the initial series of forty-two tested compounds, compound 11 (2S-2,4-dihydroxy-2-(1-hydroxy-1-methylethyl)-dihydrofuro[2,3-h]flavanone, $IC_{50}$ 0.11 µM) and compound 12 (isolicoflavonol, $IC_{50}$ 0.13 µM) were the most potent inhibitors, exhibiting an approximately 60-fold potency greater than aminoglutethimide. Compound 13 (2S-abyssinone II, $IC_{50}$ 0.37 µM) and compound 9 (3-[γ-hydroxymethyl-(E)-γ-methylallyl]-2,4,2',4'-tetrahydroxychalcone 11'-O-coumarate, $IC_{50}$ 0.52 µM) also demonstrated significant inhibitory activity.

Some of the compounds were tested for binding to the estrogen receptor -alpha or -beta. Interestingly, none of the aromatase active compounds showed significant binding to either of the receptors. This is an important property because if the estrogenic effects were potent, beneficial aromatase inhibitory effects may be overcome. Compound 11 also was effective in inhibiting (50%) the formation of alveolar lesions in a mouse mammary organ culture model when tested at 100 ng/ml. These and related compounds, therefore, are effective chemopreventive agents in preventing formation of estrogen-dependent tumors in the breast and prostate.

A comparison of activity of currently available aromatase inhibitors is provided in Table 1.

TABLE 1

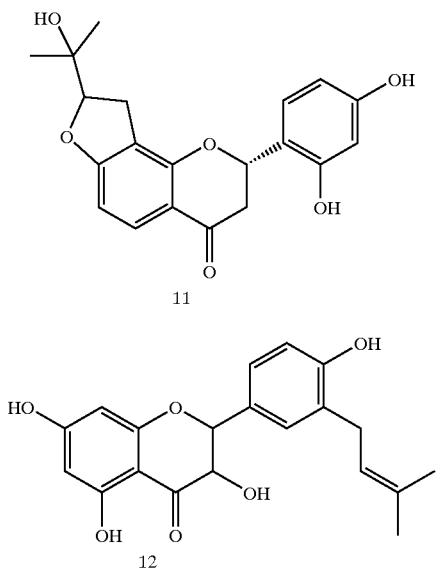

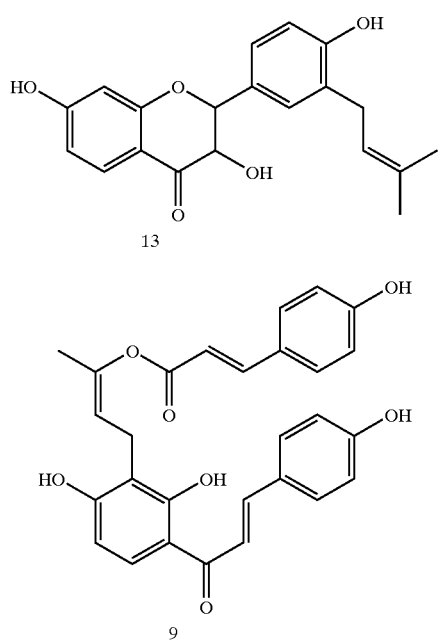

Comparison to known aromatase inhibitors

| Compound | $IC_{50}$(nM) |
| --- | --- |
| Aminoglutethimide | 600 |
| Rogletimide | 1100 |
| Vorozole | 1.4 |
| Liarozole | Unknown |
| *Broussonetia papyrifera* extract | 110 |

Compounds 11–13 and 9 isolated from the extract of *Broussonetia papyrifera* are potent inhibitors of the rate-limiting enzyme aromatase in the biosynthesis of estrogen. These compounds, related compounds, and *Broussonetia papyrifera* extract, therefore, are effective in preventing estrogen-dependent tumors of the breast or prostate through topical or systemic administration.

Compounds isolated from *B. papyrifera*, therefore, are very potent inhibitors of aromatase and are isolated from a common, natural, renewable source. While more potent inhibitors of aromatase exist, the *B. papyrifera* derived compounds are based on nonsteroidal moieties unlike any current class of inhibitors. Additionally, the compounds are natural products that have reduced toxicity, do not exhibit the disadvantages of prior aromatase inhibitors, and, therefore, should have a wider acceptance in the general population.

The above data and following tests show that *B. papyrifera* extract, and specific compounds present therein, can be administered to mammals in methods of treating various cancers. *B. papyrifera* extract, and specific compounds present therein, as active agents, can be formulated in suitable excipients for oral administration, or for parenteral administration. Such excipients are well known in the art. The active agents typically are present in such a composition in an amount of about 0.1% to about 75% by weight, either alone or in combination.

Pharmaceutical compositions containing an active agent of the present invention are suitable for administration to humans or other mammals. Typically, the pharmaceutical compositions are sterile, and contain no toxic, carcinogenic, or mutagenic compound which would cause an adverse reaction when administered.

Administration of an active agent can be performed before, during, or after exposure to a carcinogen or procarcinogen.

The method of the invention can be accomplished using an active agent as described above, or as a physiologically acceptable salt or solvate thereof. The compound, salt, or solvate can be administered as the neat compound, or as a pharmaceutical composition containing either entity.

The active agents can be administered by any suitable route, for example by oral, buccal, inhalation, sublingual, rectal, vaginal, transurethral, nasal, percutaneous, i.e., transdermal, or parenteral (including intravenous, intramuscular, subcutaneous, and intracoronary) administration. Parenteral administration can be accomplished using a needle and syringe, or using a high pressure technique, like POWDERJECT™.

The compounds and pharmaceutical compositions thereof include those wherein the active ingredient is administered in an effective amount to achieve its intended purpose. More specifically, a "therapeutically effective amount" means an amount effective to prevent development of, to cure, or to alleviate the existing symptoms of, the subject being treated. Determination of a therapeutically effective amount is well within the capability of those skilled in the art, especially in light of the detailed disclosure provided herein.

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a range of dosage for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage is determined by an individual physician in view of the patient's condition. Dosage amount and interval can be adjusted individually to provide levels of the active agent that are sufficient to maintain therapeutic or prophylactic effects.

The amount of pharmaceutical composition administered is dependent on the subject being treated, on the subject's weight, the severity of the affliction, the manner of administration, and the judgment of the prescribing physician.

Specifically, for administration to a human in the curative or prophylactic treatment of a cancer, oral dosages of an active agent generally are about 0.1 to about 1000 mg daily for an average adult patient (70 kg). Thus, for a typical adult patient, individual tablets or capsules contain 0.2 to 500 mg of an active agent, in a suitable pharmaceutically acceptable vehicle or carrier, for administration in single or multiple doses, once or several times per day. Dosages for intravenous, buccal, or sublingual administration typically are 0.1 to 500 mg per single dose as required. In practice, the physician determines the actual dosing regimen which is most suitable for an individual patient, and the dosage varies with the age, weight, and response of the particular patient.

The above dosages are exemplary of the average case, but there can be individual instances in which higher or lower dosages are merited, and such are within the scope of this invention.

An active agent of the present invention can be administered alone, but generally is administered in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of the active agents into preparations which can be used pharmaceutically.

These pharmaceutical compositions can be manufactured in a conventional manner, e.g., by conventional mixing, dissolving, granulating, dragee-making, emulsifying, encapsulating, entrapping, or lyophilizing processes. Proper formulation is dependent upon the route of administration chosen. When a therapeutically effective amount of an active agent of the present invention is administered orally, the composition typically is in the form of a tablet, capsule, powder, solution, or elixir. When administered in tablet form, the composition can additionally contain a solid carrier, such as a gelatin or an adjuvant. The tablet, capsule, and powder contain about 5% to about 95% of an active agent of the present invention, and preferably from about 25% to about 90% compound of the present invention. When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.5% to about 90% by weight of an active agent of the present invention, and preferably about 1% to about 50% of an active agent of the present invention.

When a therapeutically effective amount of an active agent of the present invention is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, in addition to a compound of the present invention, an isotonic vehicle.

Suitable active agents can be readily combined with pharmaceutically acceptable carriers well-known in the art. Such carriers enable the present compounds to be formulated as tablets, pills, dragees, capsules, liquids, gels, syrups, slurries, suspensions and the like, for oral ingestion by a patient to be treated. Pharmaceutical preparations for oral use can be obtained by adding the active agent with a solid excipient, optionally grinding a resulting mixture, and processing the mixture of granules, after adding suitable auxiliaries, if desired, to obtain tablets or dragee cores. Suitable excipients include, for example, fillers and cellulose preparations. If desired, disintegrating agents can be added.

The active agents can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of the active agents can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

The active agents also can be formulated in rectal compositions, such as suppositories or retention enemas, e.g., containing conventional suppository bases. In addition to the formulations described previously, the compounds also can be formulated as a depot preparation. Such long-acting formulations can be administered by implantation (for example, subcutaneously or intramuscularly) or by intramuscular injection. Thus, for example, the active agents can be formulated with suitable polymeric or hydrophobic materials (for example, as an emulsion in an acceptable oil) or ion exchange resins, or as sparingly soluble derivatives, for example, as a sparingly soluble salt.

In particular, an active agent can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. A compound also can be injected parenterally, for example, intravenously, intramuscularly, subcutaneously, or intracoronarily. For parenteral administration, the compound is best used in the form of a sterile aqueous solution which can contain other substances, for example, salts, or monosaccharides, such as mannitol or glucose, to make the solution isotonic with blood.

Experimentals

General Experimental Procedures. Melting points were determined on a Fisher-Johns melting point apparatus and are uncorrected. Optical rotations were obtained using a Perkin-Elmer 241 polarimeter. UV spectra were recorded with a Beckman DU-7 spectrometer. CD measurements were performed using a JASCO 600 CD spectrometer. IR spectra were collected on a JASCO 410 FT-IR spectrometer. NMR experiments were conducted on Bruker DPX-300 and Bruker DRX-500 MHz spectrometers using a 5 mm or a 2.5 mm sample tube. MS and HRMS were recorded on a Finnigan MAT 90 instrument operating at 70 eV and a HPLC-ESMS system (Hewlett-Packard 5989B mass spectrometer, 5998A electrospray interface). MALDI-TOF-MS data were obtained on a Bruker Reflex III TOF mass spectrometer. Silica gel 60 (Merck, 230–400 mesh) was used for column chromatography. HPLC was performed using a Hitachi system with a L-7100 pump and a L-7100 UV detector and a Waters system with a 515 pump and a 2487 UV detector.

Plant Material. Whole plants of *Broussonetia papyrifera* (L.) L'Hér. ex Vent. were collected at Shawnee National Forest, Harrisburg, Ill., in September 1998 and dried. A voucher specimen (accession number 2208806) has been deposited at the Field Museum of Natural History, Chicago, Ill.

Extraction and Isolation. The dried plant material (4.8 kg) was ground and extracted with MeOH (3×10 L) by maceration. The extracts were combined and concentrated in vacuo at 40° C. The concentrated extract was suspended in 90% MeOH and then partitioned with petroleum ether (3×3 L) to afford a petroleum ether-soluble syrup (D001, 43.5 g) on drying. Next, the aqueous methanol extract was concentrated and suspended in $H_2O$ (2 L) and partitioned again with EtOAc (3×2 L) to give an EtOAc-soluble extract (D002, 64.8 g) and an aqueous residue (D003, 170.0 g). The EtOAc-soluble extract significantly inhibited aromatase activity (D002, 74% inhibition at 80 μg/mL; D001, 27% inhibition; D003, 14% inhibition).

Fractionation of the EtOAc-soluble extract (D002) was initiated by vacuum-liquid chromatography over Si gel as stationary phase using a $CHCl_3$-MeOH gradient as mobile phase to afford 13 pooled fractions (F001–F013). Of these, F005–F007 showed the most potent aromatase inhibitory activity (94–95% inhibition at 80 μg/mL), and were worked-up separately. Thus, F005 (eluted with $CHCl_3$-MeOH (40:1); 94% inhibition at 80 μg/mL) was eluted on Si gel with gradient mixtures of $CHCl_3$-MeOH to afford fractions F014–F021. Of these, F018 (eluted with $CHCl_3$-MeOH (30:1); 50% inhibition at 8 μg/mL) was chromatographed over Si gel with petroleum ether-EtOAc (20:1→2:1) resulting in the isolation of broussoflavonol F (16, 30 mg, 0.00063%)[16] and marmesin (12 mg, 0.00025%).[18] Additional chromatographic separation of a fraction eluted by petroleum ether-EtOAc (10:1) over MCI-gel CHP 20P (Supleco, Bellefonte, Pa.) using a $H_2O$-MeOH gradient, yielded broussochalcone B (2 mg, 0.000042%)[22] and isobavachalcone (2.5 mg, 0.000052%).[48] Further separation of an impure fraction eluted by petroleum ether-EtOAc (9:1), by HPLC (YMC ODS-AQ Pack (YMC, Wilmington, N. C.), 250×20 mm i. d., 85% MeOH in $H_2O$, flow rate 7 mL/min) resulted in the purification of 1-(4-hydroxy-2-methoxyphenyl)-3-(4-hydroxy-3-prenylphenyl)propane (7, $t_R$ 16 min, 2.5 mg, 0.000052%). F019 (eluted with $CHCl_3$-MeOH (20:1); 51% inhibition at 8 μg/mL) was chromatographed on a Si gel column developed with petroleum ether-EtOAc (15:1 to 2:1) to afford fractions F022–F031. (3S, 5R)-Loliolide (7 mg, 0.00015%)50 was crystallized from F031 (petroleum ether-EtOAc, 1:1). F028 (eluted with petroleum ether-EtOAc (10:1); 77% inhibition at 8 μg/mL) was passed over a column containing Sephadex LH-20 (Sigma, St. Louis, Mo.) using MeOH for elution, resulting in two separate fractions. From the latter fraction, broussonin B (8 mg, 0.00017%)18 was obtained. Further purification of the first fraction was carried by HPLC (YMC ODS-AQ Pack, 250×20 mm i. d., 80% MeCN in $H_2O$, flow rate 7 mL/min) to afford (2S)-naringenin (17, $t_R$ 11 min, 1.6 mg, 0.000033%),[38] (2S)-abyssinone II (13, $t_R$ 20 min, 0.5 mg, 0.00001%),[35] and bavachin ($t_R$ 22 min, 0.3 mg, 0.0000063%).[44] F029 (eluted with petroleum ether-EtOAc (8:1); 83% inhibition at 8 μg/mL) was further chromatographed on TSK-gel Toyopearl HW 40F (Supleco, Bellefonte, Pa.) using a $H_2O$-MeOH gradient resulting in the isolation of broussonin A (18, 3 mg, 0.000063%),[18] (2R, 3R)-lespedezaflavanone C (1.3 mg, 0.000027%),[43] and moracins D (1.3 mg, 0.000027%)[49] and I (5.5 mg, 0.00015).[31] The impure fraction eluted with 70% MeOH in $H_2O$ was subjected to preparative TLC using a $CHCl_3$-MeOH (20:1)

to afford (2S)-7,4'-dihydroxyflavan (1.1 mg, 0.000023%),[20] and broussonins E (2 mg, 0.000042%)[20] and F (1 mg, 0.000021%).[20] F030 (eluted with petroleum ether-EtOAc (5:1); 59% inhibition at 8 μg/mL) was subjected to passage over $C_{18}$ reversed-phase Si gel (Sigma, St. Louis, Mo.) using 70% MeOH in $H_2O$ resulting in the purification of (2S)-7, 4'-dihydroxy-3'-prenylflavan (4, 10 mg, 0.00021%), (2S)-2', 4'-dihydroxy-7-methoxy-8-prenylflavan (22, 5 mg, 0.0001%),[42] and 1-(2,4-dihydroxy-3-prenylphenyl)-3-(4-hydroxyphenyl)propane (6, 3.5 mg, 0.000073%).

Fraction F006 (eluted with $CHCl_3$-MeOH (30:1); 95% inhibition at 80 μg/mL) was chromatographed on Si gel with gradient mixtures of $CHCl_3$-MeOH resulting in the preparation of fractions F032–F041. Then, F037 (eluted with $CHCl_3$-MeOH (30:1); 66% inhibition at 8 μg/mL) was further chromatographed on TSK-gel Toyopearl HW 40F using MeOH, producing subfractions F042–F049. F043, F044, F047, and F048 were purified on $C_{18}$ reversed-phase Si gel using a $H_2O$-MeOH gradient leading to the isolation of 5,7-dihydroxycoumarin (3 mg, 0.000063%),52 (2R,3R) katuranin (6.5 mg, 0.00014%),[45] moracin N (20, 4 mg, 0.000083%),[40] and 2,4,2',4'-tetrahydroxy-3'-prenylchalcone (19, 8 mg, 0.00017%),[39] respectively. F045 and F046 was purified using HPLC (YMC ODS-AQ Pack, 250×20 mm i.d., 60% MeCN in $H_2O$, flow rate 7 mL/min) resulting in the purification of dimethylmoracin I (10, $t_R$ 15 min, 2.5 mg, 0.000052%), (2S)-2',4'-dihydroxy-2"-(1-hydroxy-1-methylethyl)-dihydrofuro[2,3-h]flavanone (11, $t_R$ 19 min, 0.5 mg, 0.00001%), 5,7,3',4'-tetrahydroxy-3-methoxy-6-geranylflavone (3, $t_R$ 11 min, 3 mg, 0.000063%), and 5,7, 2',4'-tetrahydroxy-3-geranylflavone (1, $t_R$ 12 min, 2 mg, 0.000042%), respectively. F038 (eluted with $CHCl_3$-MeOH (20:1); 61% inhibition at 8 μg/mL) was subjected to passage over Sephadex LH-20 using MeOH resulting in pooled fractions F050–F059. trans-Resveratrol (12 mg, 0.00025%)[51] was crystallized from F051. F052 (62% inhibition at 4 μg/mL) was further purified by $C_{18}$ reversed-phase Si gel using 50% MeOH in $H_2O$ resulting in the purification of (2S)-5,7,2',4'-tetrahydroxyflavanone (14, 5 mg, 0.0001%),[36] 5,7,3',4'-tetrahydroxy-6-geranylflavonol (2, 3.5 mg, 0.000073%), and 1-(2,4-dihydroxyphenyl)-3-(4-hydroxyphenyl)propane (5, 4 mg, 0.000083%). F054 (67% inhibition at 4 μg/mL) was purified by HPLC (YMC ODS-AQ Pack, 250×20 mm i.d., 50% MeCN in $H_2O$, flow rate 5 mL/min) leading to the isolation of euchrenone a7 (15, $t_R$ 20 min, 1.1 mg, 0.000023%),[37] gancaonin P ($t_R$ 29 min, 2 mg, 0.000042%),[46] and broussochalcone A ($t_R$ 42 min, 0.9 mg, 0.000019%).[22] F055 (72% inhibition at 4 μg/mL) was chromatographed over $C_{18}$ reversed-phase Si gel using 40% MeOH in $H_2O$, resulting in pure moracin M (4 mg, 0.000083%)31 and 2,4,2',4'-tetrahydroxychalcone (1 mg, 0.000021%).[39]

Fraction F007 (eluted with $CHCl_3$-MeOH (20:1); 94% inhibition at 80 μg/mL) was eluted on Sephadex LH-20 using a $H_2O$—MeOH gradient producing fractions F060–F064. F062 (eluted with 60% MeOH in $H_2O$; 75% inhibition at 4 μg/mL) was purified using HPLC (YMC ODS-AQ Pack, 250×20 mm i.d., 50% MeCN in $H_2O$, flow rate 5 mL/min) to afford pure 3'-(γ-hydroxymethyl-(E)-γ-methylallyl)-2,4,2',4'-tetrahydroxychalcone 11'-O-coumarate (9, $t_R$ 27 min, 2 mg, 0.000042%), isogemichalcone C (8, $t_R$ 31 min, 1.5 mg, 0.000031%), and isolicoflavonol (12, $t_R$ 38 min, 0.8 mg, 0.000017%).[34] F063 (eluted with 80% MeOH in $H_2O$; 76% inhibition at 4 μg/mL) was purified using HPLC (YMC ODS-AQ Pack, 250×20 mm i.d., 30% MeCN in $H_2O$, flow rate 5 mL/min) resulting in the purification of (2R,3R)-5,7,2',4'-tetrahydroxyflavanonol ($t_R$ 11 min, 3.5 mg, 0.000073%)[47] and albanol A (21, $t_R$ 21 min, 3.7 mg, 0.000077%).[41]

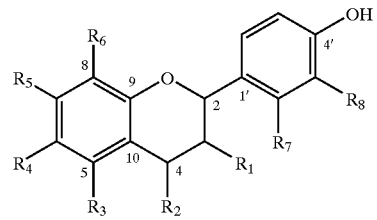

1  $R_1$ = Geranyl, $R_2$ = ═O, $R_3$ = OH, $R_4$ = H, $R_5$ = OH, $R_6$ = H, $R_7$ = OH, $R_8$ = H, $\Delta^{2(3)}$ 2  $R_1$ = OH, $R_2$ = ═O, $R_3$ = OH, $R_4$ = Geranyl, $R_5$ = OH, $R_6$ = H, $R_7$ = H, $R_8$ = OH, $\Delta^{2(3)}$ 3  $R_1$ = $OCH_3$, $R_2$ = ═O, $R_3$ = OH, $R_4$ = Geranyl, $R_5$ = OH, $R_6$ = H, $R_7$ = H, $R_8$ = OH, $\Delta^{2(3)}$ 4  $R_1$ = $H_2$, $R_2$ = $H_2$, $R_3$ = H, $R_4$ = H, $R_5$ = OH, $R_6$ = H, $R_7$ = H, $R_8$ = Prenyl 12  $R_1$ = OH, $R_2$ = ═O, $R_3$ = OH, $R_4$ = H, $R_5$ = OH, $R_6$ = H, $R_7$ = H, $R_8$ = Prenyl, $\Delta^{2(3)}$ 13  $R_1$ = $H_2$, $R_2$ = ═O, $R_3$ = H, $R_4$ = H, $R_5$ = OH, $R_6$ = H, $R_7$ = H, $R_8$ = Prenyl 14  $R_1$ = $H_2$, $R_2$ = ═O, $R_3$ = OH, $R_4$ = H, $R_5$ = OH, $R_6$ = H, $R_7$ = OH, $R_8$ = H 15  $R_1$ = $H_2$, $R_2$ = ═O, $R_3$ = H, $R_4$ = H, $R_5$ = OH, $R_6$ = Prenyl, $R_7$ = OH, $R_8$ = H 16  $R_1$ = OH, $R_2$ = ═O, $R_3$ = OH, $R_4$ = H, $R_5$ = OH, $R_6$ = Prenyl, $R_7$ = H, $R_8$ = Prenyl, $\Delta^{2(3)}$ 17  $R_1$ = $H_2$, $R_2$ = ═O, $R_3$ = OH, $R_4$ = H, $R_5$ = OH, $R_6$ = H, $R_7$ = H, $R_8$ = H 22  $R_1$ = $H_2$, $R_2$ = $H_2$, $R_3$ = H, $R_4$ = H, $R_5$ = $OCH_3$, $R_6$ = Prenyl, $R_7$ = OH, $R_8$ = H Geranyl:

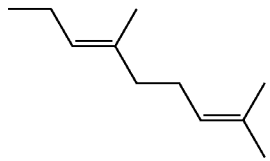

Prenyl:

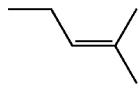

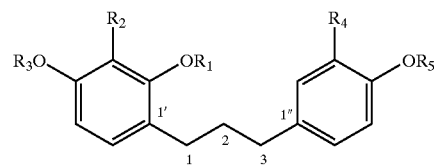

5  $R_1$ = H, $R_2$ = H, $R_3$ = H, $R_4$ = H, $R_5$ = H

6  $R_1$ = H, $R_2$ = Prenyl, $R_3$ = H, $R_4$ = H, $R_5$ = H

7  $R_1$ = $CH_3$, $R_2$ = H, $R_3$ = H, $R_4$ = Prenyl, $R_5$ = H

18  $R_1$ = H, $R_2$ = H, $R_3$ = $CH_3$, $R_4$ = H, $R_5$ = H

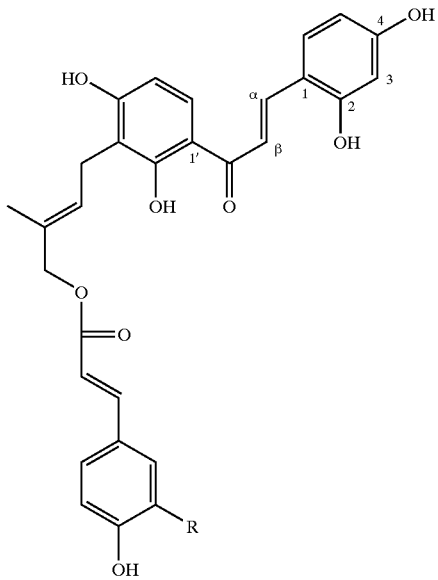

8 R = OCH₃
9 R = H

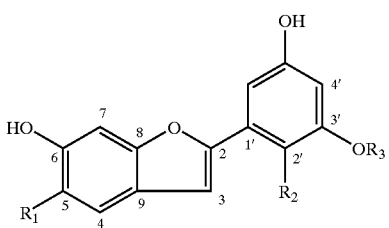

10 R₁ = H, R₂ = Prenyl, R₃ = H
20 R₁ = Prenyl, R₂ = H, R₃ = H

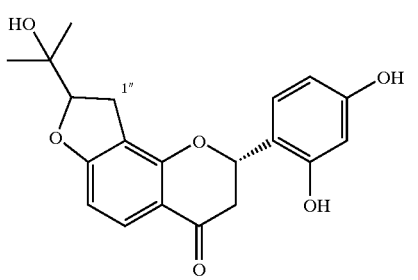

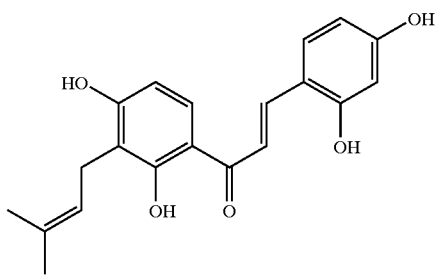

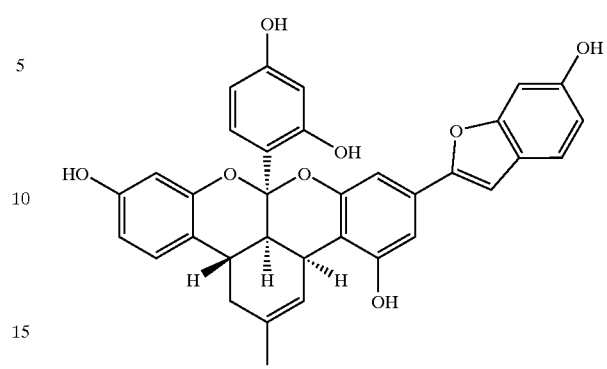

5,7,2',4'-Tetrahydroxy-3-geranylflavone (1). Brown powder; mp 94–95° C.; UV (MeOH) $\lambda_{max}$ (log ε) 314 (4.16), 258 (4.40), 207 (4.78) nm; IR (NaCl) $\gamma_{max}$ 3335, 2922, 1652, 1507, 1163 cm⁻¹; ¹H and ¹³C NMR data, see Table 1; HMBC correlations: H-6/C-7, C-8, C-10; H-8/C-6, C-7, C-9, C-10; H-3'/C-1', C-2', C-4', C-5'; H-5'/C-1', C-3'; H-6'/C-2, C-2'; H-1"/C-2, C-3, C-4; OH-5/C-5, C-6, C-10; NOESY correlations: H-6'/H-1"; H-2"/H-4"; H-7"/H-9"; EIMS m/z 422 (M⁺, 45), 353 (100), 311 (31), 299 (51), 297 (51), 153 (38), 149 (25); HREIMS m/z 422.1719, calcd for $C_{25}H_{26}O_6$, 422.1729.

5,7,3',4'-Tetrahydroxy-6-geranylflavonol (2). Brown powder; mp 158–156° C.; UV (MeOH) $\lambda_{max}$ (log ε) 376 (4.34), 258 (4.34), 206 (4.66) nm; IR (NaCl) $\gamma_{max}$ 3365, 2920, 1652, 1540 cm⁻¹; ¹H and ¹³C NMR data, see Table 1; HMBC correlations: H-2'/C-2, C-4', C-6'; H-5'/C-1', C-3'; H-6'/C-2, C-2', C-4'; H-1"/C-5, C-6, C-7, C-2", C-3"; OH-5/C-5, C-6, C-10; NOESY correlations: H-2"/H-4"; H-7"/H-9"; EIMS m/z 438 (M⁺, 45), 369 (84), 353 (25), 315 (100), 143 (35); HREIMS m/z 438.1683, calcd for $C_{25}H_{26}O_7$, 438.1679.

5,7,3',4'-Tetrahydroxy-3-methoxy-6-geranylflavone (3). Brown powder; mp 98–99° C.; UV (MeOH) $\lambda_{max}$ (log ε) 351 (4.11), 270 (4.11), 260.5 (4.13), 205 (4.50) nm; IR (NaCl) $\gamma_{max}$ 3362, 2925, 1646, 1472 cm 1; ¹H and ¹³C NMR data, see Table 1; HMBC correlations: H-8/C-6, C-7, C-9, C-10; H-2'/C-2, C-4', C-6'; H-5'/C-1', C-3'; H-6'/C-2, C-2', C-4'; H-1"/C-5, C-6, C-7, C-2", C-3"; OCH₃/C-3; OH-5/C-5, C-6, C-10; NOESY correlations: OCH₃/H-2'; H-1"/H-5"; H-2"/H-4"; H-7"/H-9"; EIMS m/z 452 (M⁺, 46), 409 (7), 383 (99), 329 (100), 137 (16); HREIMS m/z 452.1833, calcd for $C_{26}H_{28}O_7$, 452.1835.

(2S)-7,4'-Dihydroxy-3'-prenylflavan (4). Brown powder; mp 116–117° C.; $[\alpha]_D^{20}$ -4.90 (c 0.25, MeOH); UV (MeOH) $\lambda_{max}$ (log ε) 305 (3.10), 283 (3.40), 207 (4.28) nm; CD (MeOH) nm AC₂₈₂-10.9; IR (NaCl) $\gamma_{max}$ 3364, 2920, 1617, 1507 cm⁻¹; ¹H and ¹³C NMR data, see Table 2; HMBC correlations: H-2/C-3, C-4, C-9, C-1', C-2', C-6'; H-3/C-2, C-4, C-1'; H-4/C-2, C-3, C-5, C-9; H-5/C-4, C-7, C-9; H-6/C-7, C-8, C-10; H-8/C-6, C-9, C-10; H-2'/C-2, C-4', C-6', C-1"; H-5'/C-1¹, C-3', C-4', C-6'; H-6'/C-2, C-2', C-4'; H-1"/C-3', C-2", C-3"; H-2"/C-4", C-5"; EIMS m/z 310 (M⁺, 100), 188 (80), 175 (37), 133 (50); HREIMS m/z 310.1564, calcd for $C_{20}H_{22}O_3$, 310.1568.

1-(2,4-Dihydroxyphenyl)-3-(4-hydroxyphenyl)propane (5). Brown powder; mp 92–93° C.; UV (MeOH) $\lambda_{max}$ (log ε) 280 (3.59), 224 (4.07), 205.5 (4.28) nm; IR (NaCl) $\gamma_{max}$ 3335, 2929, 1615, 1511 cm$^{-1}$; $^1$H and $^{13}$C NMR data, see Table 3; HMBC correlations: H-1/C-2, C-1', C-2'; H-2/C-1, C-3, C-1', C-1"; H-3/C-2, C-1", C-2"; H-3'/C-1', C-2', C-5'; H-5'/C-1', C-3', C-4'; H-6'/C-1, C-2'; H-2"/C-3, C-3", C-4"; H-3"/C-1", C-4"; EIMS m/z 244 (M$^+$, 68), 134 (23), 123 (100), 107 (32); HREIMS m/z 244.1098, calcd for $C_{15}H_{16}O_3$, 244.1099.

1-(2,4-Dihydroxy-3-prenylphenyl)-3-(4-hydroxyphenyl)propane (6). Brown powder; mp 115–116° C.; UV (MeOH) $\lambda_{max}$ (log ε) 279 (3.28), 232 (3.55) nm; IR (NaCl) $\gamma_{max}$ 3421, 2909, 1652, 1515 cm$^{-1}$; $^1$H and $^{13}$C NMR data, see Table 3; HMBC correlations: H-1/C-1', C-2$^1$, C-6$^1$; H-2/C-1', C-1"; H-3/C-1", C-2"; H-5'/C-1', C-3', C-4'; H-6'/C-1, C-2', C-4'; H-2"/C-3, C-1", C-4"; H-3"/C-1", C-4"; H-1'''/C-2', C-4$^1$; H-4''' and H-5'''/C-2''', C-3'''; EIMS m/z 312 (M$^+$, 67), 257 (12), 191 (100), 135 (74); HREIMS m/z 312.1725, calcd for $C_{20}H_{24}O_3$, 312.1725.

1-(4-Hydroxy-2-methoxyphenyl)-3-(4-hydroxy-3-prenylphenyl)propane (7). Brown powder; mp 85–86° C.; UV (MeOH) $\lambda_{max}$ (log ε) 281 (3.59), 228 (3.97) nm; IR (NaCl) $\gamma_{max}$ 3420, 2925, 1651, 1507 cm$^{-1}$; $^1$H and $^{13}$C NMR data, see Table 3; HMBC correlations: H-1/C-2, C-1', C-2'; H-2/C-1, C-3, C-1', C-1"; H-3/C-2, C-1", C-6"; H-3'/C-1', C-2', C-4', C-5'; H-5'/C-1', C-3', C-4'; H-6'/C-1, C-2$^1$; H-2"/C-1''', C-4''', C-1"; H-5"/C-4"; H-6"/C-3, C-4"; H-1'''/C-2", C-3", C-4", C-2'''; H-2'''/C-1''', C-4''', C-5'''; OCH$_3$/C-2'; EIMS m/z 326 (M$^+$, 66), 175 (41), 137 (100); HREIMS m/z 326.1877, calcd for $C_{21}H_{26}O_3$, 326.1881.

Isogemichalcone C (8). Orange powder; UV (MeOH) $\lambda_{max}$ (log ε) 386 (4.40), 321 (4.39), 206 (4.65) nm; IR (NaCl) $\gamma_{max}$ 3267, 2922, 1676, 1599, 1492, 1368, 1242, 1176 cm$^{-1}$; $^1$H NMR (CD$_3$COCD$_3$, 500 MHz) δ 1.88 (3H, s, H-10'), 3.46 (2H, d, J=7.4 Hz, H-7'), 3.91 (3H, s, OCH$^3$), 4.54 (2H, s, H-11'), 5.69 (1H, brt, J=8.0 Hz, H-8'), 6.40 (1H, d, J=15.9 Hz, H-8"), 6.45 (1H, brd, J=8.5 Hz, H-5), 6.51 (1H, brs, H-3), 6.53 (1H, d, J=8.9 Hz, H-5'), 6.85 (1H, d, J=8.1 Hz, H-5"), 7.12 (1H, dd, J=1.7 and 8.2 Hz, H-6"), 7.34 (1H, d, J=1.6 Hz, H-2"), 7.57 (1H, d, J=16.0 Hz, H-7"), 7.68 (1H, d, J=8.5 Hz, H-6), 7.80 (1H, d, J=15.4 Hz, H-1), 7.91 (1H, d, J=8.8 Hz, H-6'), 8.22 (1H, d, J=15.4 Hz, H-β); $^{13}$C NMR (CD$_3$COCD$_3$, 125 MHz) δ 14.2 (C-10'), 22.0 (C-7'), 56.3 (OCH$_3$), 70.2 (C-11'), 103.6 (C-3) 107.9 (C-5') 109.1 (C-5), 111.2 (C-2"), 114.5 (C-1'), 115.0 (C-3'), 115.2 (C-1), 115.8 (C-8"), 116.0 (C-5"), 117.5 (C-α), 124.0 (C-6'), 127.5 (C-1"), 127.7 (C-8'), 130.2 (C-6'), 131.2 (C-9'), 131.7 (C-6), 140.9 (C-β), 145.6 (C-7"), 148.7 (C-3"), 150.0 (C-4"), 159.9 (C-2), 162.3 (C-4), 162.5 (C-4'), 165.1 (C-2') 167.3 (C-9"), 193.4 (CO); HMBC correlations: H-6/C-β H-α/CO; H-β/CO; H-6'/CO; H-7'/C-2', C-3', C-4'; H-11'/C-9"; NOESY correlations: H-7'/H-10'; H-8,'/H-11'; H-2"/OCH$_3$; FABMS m/z 555 [M+Na]+, 479 (25), 329 (100), 307 (22), 284 (15), 198 (50); HRFABMS m/z 555.1577, calcd for $C_{30}H_{28}O_9Na$, 555.1623.

3'-[γ-Hydroxymethyl-(E)-γ-methylallyl]-2,4,2',4'-tetrahydroxychalcone 11'-O-coumarate (9). Orange powder; UV (MeOH) $\lambda_{max}$ (log ε) 387 (4.28), 312 (4.39), 207 (4.56) nm; IR (NaCl) $\gamma_{max}$ 3160, 2923, 1674, 1602, 1444, 1368, 1240, 1168, 1109 cm$^{-1}$; $^1$H NMR (CD$_3$COCD$_3$, 500 MHz) δ 1.88 (3H, s, H-10'), 3.46 (2H, d, J=7.1 Hz, H-7'), 4.55 (2H, s, H-11'), 5.68 (1H, brt, J=7.0H-9'), 6.35 (1H, d, J=16.0 Hz, H-8"), 6.45 (1H, brd, J=8.4 Hz, H-5), 6.51 (1H, brs, H-3), 6.53 (1H, d, J=8.8 Hz, H-5'), 6.87 (2H, d, J=8.5 Hz, H-3" and H-5"), 7.54 (2H, d, J=8.6 Hz, H-2" and H-6"), 7.59 (1H, d, J=16.0 Hz, H-7"), 7.69 (1H, d, J=8.5 Hz, H-6), 7.79 (1H, d, J=15.4 Hz, H-α), 7.90 (1H, d, J=8.9 Hz, H-6'), 8.21 (1H, d, J=15.4 Hz, H-β); $^{13}$C NMR (CD$_3$COCD$_3$, 125 MHz) δ 14.2 (C-10'), 22.0 (C-7'), 70.2 (C-11'), 103.6 (C-3) 107.8 (C-5'), 109.1 (C-5), 114.5 (C-1'), 115.0 (C-3'), 115.2 (C-1), 115.6 (C-8"), 116.6 (C-3" and C-5"), 117.4 (C-*), 127.0 (C-1"), 127.7 (C-8'), 130.2 (C-6'), 130.9 (C-2" and C-6"), 131.2 (C-9'), 131.7 (C-6), 140.9 (C-β), 145.3 (C-7"), 159.9 (C-2), 160.5 (C-4"), 162.3 (C-4'), 162.5 (C-4), 165.1 (C-2'), 167.3 (C-9"), 193.4 (CO); HMBC correlations: H-6/C-β H-α/CO; H-β/CO; H-6'/CO; H-7'/C-2', C-3', C-4'; H-11'/C-9"; FABMS m/z 525 [M+Na]+, 460 (35), 307 (100), 289 (95), 273 (43), 242 (30); HRFABMS m/z 525.1484, calcd for $C_{29}H_{26}O_8Na$, 525.1518.

Demethylmoracin I (10). Brown powder; mp 82–83° C.; UV (MeOH) $\lambda_{max}$ (log ε) 310 (4.30), 214 (4.47) nm; IR (NaCl) $\gamma_{max}$ 3364, 2924, 1621, 1488, 1145 cm$^{-1}$; $^1$H NMR (CD$_3$OD, 500 MHz) δ 1.64 (6H, s, H-4" and H-5"), 3.42 (2H, d, J=6.3 Hz, H-1"), 5.13 (1H, m, H-2"), 6.33 (1H, d, J=2.5 Hz, H-4'), 6.61 (1H, d, J=2.5 Hz, H-2'), 6.66 (1H, s, H-3), 6.72 (1H, dd, J=2.2 and 8.4 Hz, H-5), 6.87 (1H, d, J=2.1 Hz, H-7), 7.33 (1H, d, J=8.4 Hz, H-4); $^{13}$C NMR (CD$_3$OD, 125 MHz) δ 18.1 (C-4"), 25.9 (C-5"), 26.0 (C-1"), 98.4 (C-7), 103.8 (C-4'), 105.5 (C-3), 113.0 (C-5 and C-2'), 119.3 (C-1'), 121.9 (C-4), 123.0 (C-9), 125.7 (C-2"), 131.4 (C-3"), 133.0 (C-6'), 156.2 (C-3'), 156.6 (C-2), 156.9 (C-8), 157.0 (C-6), 157.9 (C-5'); HMBC correlations: H-3/C-2, C-9; H-2'/C-2, C-1', C-4'; H-1"/C-1', C-5', C-6'; EIMS m/z 310 (M$^+$, 100), 295 (37), 267 (55), 188 (67), 123 (26); HREIMS m/z 310.1208, calcd for $C_{21}H_{26}O_3$, 310.1205.

2S-2',4'-Dihydroxy-2"-(1-hydroxy-1-methylethyl)-dihydrofuro[2,3-h]flavanone (11). Yellow powder; UV (MeOH) $\lambda_{max}$ (log ε) 387 (3.23), 297 (3.30), 284.5 (3.38), 219 (3.82) nm; CD nm (MeOH) AC$_{294}$-7.2; IR (NaCl) $\gamma_{max}$ 3228, 2923, 1683 cm$^{-1}$; $^1$H and $^{13}$C NMR, see Table 2; HMBC correlations: H-2/C-2', C-6'; H-3/C-2, C-4; H—S/C-4, C-7, C-9; H-6/C-7, C-8; H-3'/C-2', C-4', C-5'; H-5'/C-1', C-3'; H-6'/C-2, C-2', C-4'; H-1"/C-7, C-8, C-9, C-2", C-3"; H-2"/C-7, C-4", C-5"; FABMS m/z 357 [M+H]+, 307 (40), 253 (15), 176 (80), 154 (100), 119 (95), 90 (85); HRFABMS m/z 357.1327, calcd for C20H21O6, 357.1332.

Isolicoflavonol (12). Yellow powder; UV (MeOH) $\lambda_{max}$ (log ε) 367 (3.72), 268 (3.77), 205 (4.23) nm; IR (NaCl) $\gamma_{max}$ 3241, 2921, 1600, 1491, 1274, 1167 cm$^{-1}$; $^1$H NMR (CD$_3$COCD$_3$, 500 MHz) δ 1.74 (3H, s, H-5"), 1.76 (3H, s, H-4"), 3.40 (2H, d, J=7.2 Hz, H-1"), 5.39 (1H, brt, J=7.3 Hz, H-2"), 6.27 (1H, s, H-6), 6.51 (1H, s, H-8), 7.00 (1H, d, J=8.1 Hz, H-5'), 7.98 (1H, brd, J=7.0 Hz, H-6'), 8.06 (1H, d, J=1.8 Hz, H-2'); FABMS m/z 353 [M–H]$^-$, 305 (45), 199 (25), 153 (100), 122 (18).

(2S)-Abyssinone II (13). Bright yellow powder; UV (MeOH) $\lambda_{max}$ (log ε) 311 (3.41), 275 (3.71), 233 (3.85), 213 (4.02) nm; CD (MeOH) nm Δε$_{272}$–1.8; IR (NaCl) $\gamma_{max}$ 3300, 2934, 1678, 1558 cm$^{-1}$; $^1$H NMR (CD$_3$OD, 500 MHz) δ 1.70 (3H, s, H-4"), 1.73 (3H, s, H-5"), 2.67 (1H, dd, J=3.0 and 16.9 Hz, H-3), 3.01 (1H, dd, J=12.8 and 16.9 Hz, H-3), 3.30 (1H, overlapped, H-1"), 5.30 (1H, m, H-2"), 5.34 (1H, dd, J=3.2 and 13.0 Hz, H-2), 6.32 (1H, d, J=2.2 Hz, H-8), 6.47 (1H, dd, J=2.3 and 8.7 Hz, H-6), 6.76 (1H, d, J=8.2 Hz, H-5'), 7.12 (1H, dd, J=2.2 and 8.2 Hz, H-6'), 7.15 (1H, d, J=2.0 Hz, H-2'), 7.70 (1H, d, J=8.7 Hz, H-5); $^{13}$C NMR (CD$_3$OD, 125 MHz) δ 17.6 (C-5"), 26.0 (C-4"), 29.3 (C-1"), 45.0 (C-3), 81.2 (C-2), 103.9 (C-5), 112.0 (C-6), 114.6 (C-10), 115.7 (C-8), 123.8 (C-2"), 126.2 (C-6'), 129.0 (C-2'), 129.2 (C-3'), 129.8 (C-5'), 131.2 (C-1'), 133.2 (C-3"), 156.9 (C-4'), 165.7 (C-9), 167.4 (C-7), 193.6 (C-4); EIMS m/z 324 (M$^+$, 94), 267 (46), 239 (31), 175 (79), 137 (100).

(2S)-5,7,2',4'-Tetrahydroxyflavanone (14). Needles; mp 258–259° C.; [α]$_D^{20}$+2.5° (c 0.32, MeOH); UV (MeOH)

$\lambda_{max}$ (log ε) 318 (3.79), 287 (4.25), 223 (4.36), 209 (4.47) nm; CD (MeOH) nm $\Delta\epsilon_{293}$ −10.2; IR (NaCl) $\gamma_{max}$ 3336, 2928, 1645, 1520 cm$^{-1}$; $^1$H NMR (CD$_3$OD, 300 MHz) δ 2.70 (1H, dd, J=2.9 and 17.2 Hz, H-3), 3.07 (1H, dd, J=13.0 and 17.2 Hz, H-3), 5.61 (1H, dd, J=2.8 and 13.0 Hz, H-2), 5.88 (1H, d, J=1.9 Hz, H-6), 5.91 (1H, d, J=1.9 Hz, H-8), 6.33 (1H, overlapped, H-3'), 6.35 (1H, overlapped, H-5'), 7.23 (1H, d, J=8.6 Hz, H-6'); $^{13}$C NMR (CD$_3$OD, 75 MHz) δ 43.1 (C-3), 75.9 (C-2), 96.1 (C-8), 96.9 (C-6), 103.3 (C-10), 103.4 (C-3'), 107.8 (C-5'), 117.9 (C-1'), 128.9 (C-6'), 156.8 (C-2'), 159.7 (C-4'), 165.4 (C-5), 168.3 (C-7), 198.5 (C-4); EIMS m/z 288 (M$^+$, 12), 270 (100), 153 (68), 136 (21).

(2S)-Euchrenone a7 (15). Bright yellow powder; UV (MeOH) $\lambda_{max}$ (log ε) 286 (3.99), 207 (4.41) nm; $^1$H NMR (CD$_3$COCD$_3$, 500 MHz) δ 1.61 (3H, s, H-4''), 1.65 (3H, s, H-5''), 2.72 (1H, dd, J=3.0 and 16.7 Hz, H-3), 2.95 (1H, dd, J=13.3 and 17.0 Hz, H-3), 3.34 (1H, brd, H-1''), 5.26 (1H, m, H-2''), 5.69 (1H, brd, J=10.3 Hz, H-2), 6.43 (1H, brd, J=8.4 Hz, H-5'), 6.48 (1H, brd, H-3'), 6.62 (1H, d, J=8.6 Hz, H-6), 7.36 (1H, d, J=8.5 Hz, H-6'), 7.59 (1H, d, J=8.6 Hz, H-5); EIMS m/z 324 (M$^+$, 9), 322 (24) 279 (47), 191 (19), 205 (10), 176 (14), 161 (26), 149 (43), 45 (100).

Broussoflavonol F (16). Yellow powder; mp 145–146° C.; UV (MeOH) $\lambda_{max}$ (log ε) 375 (4.26), 271 (4.31), 206 (4.64) nm; IR (NaCl) $\gamma_{max}$ 3364, 2923, 1651, 1558, 1507 cm$^{-1}$; $^1$H NMR (CD$_3$OD, 300 MHz) δ 1.67 (3H, s, H-5'''), 1.74 (3H, s, H-4'''), 1.76 (3H, s, H-5''''), 1.79 (3H, s, H-4''), 3.34 (2H, d, J=6.8 Hz, H-1'''), 3.49 (2H, d, J=6.7 Hz, H-1''), 5.26 (1H, m, H-2''), 5.36 (1H, m, H-2''''), 6.22 (1H, s, H-6), 6.85 (1H, d, J=8.4 Hz, H-5'), 7.98 (1H, brs, H-2'), 8.01 (1H, overlapped, H-6'); $^{13}$C NMR (CD$_3$OD, 75 MHz) δ 17.9 (C-4''''), 18.2 (C-4''), 22.5 (C-1''), 26.02 (C-5''''), 26.04 (C-5''), 29.2 (C-1''''), 98.8 (C-6), 104.5 (C-10), 107.6 (C-8), 115.6 (C-5'), 123.5 (C-2''''), 123.9 (C-2''), 124.0 (C-1'), 128.5 (C-6'), 129.5 (C-3'), 130.0 (C-2'), 132.5 (C-3''), 133.8 (C-3''''), 136.9 (C-3), 148.3 (C-2), 155.4 (C-9), 158.4 (C-4'), 160.1 (C-5), 162.7 (C-7), 177.6 (C-4); EIMS m/z 422 (M$^+$, 100), 407 (29), 367 (21), 354 (10).

(2S)-Naringenin (17). Colorless needles; $[\alpha]_D^{20}$ −7.3° (c 0.15, MeOH); UV (MeOH) $\lambda_{max}$ (log ε) 288 (3.79), 226 (3.93), 216 (3.92) nm; CD (MeOH) nm $\Delta\epsilon_{271}$ −5.5; IR (NaCl) $\gamma_{max}$ 3350, 2927, 1636, 1558 cm$^{-1}$; $^1$H NMR (CD$_3$OD, 500 MHz) δ 2.69 (1H, dd, J=2.9 and 17.1 Hz, H-3), 3.10 (1H, dd, J=13.0 and 17.2 Hz, H-3), 5.33 (1H, dd, J=2.9 and 12.9 Hz, H-2), 5.87 (1H, d, J=2.2 Hz, H-6), 5.88 (1H, d, J=2.2, 8.7 Hz, H-8), 6.80 (2H, d, J=8.6 Hz, H-3'), 7.30 (2H, d, J=8.4 Hz, H-2'); $^{13}$C NMR (CD$_3$OD, 125 MHz) δ 42.6 (C-3), 79.1 (C-2), 94.8 (C-8), 95.7 (C-6), 101.9 (C-10), 114.9 (C-3'), 127.6 (C-2'), 129.7 (C-1'), 157.6 (C-4'), 163.5 (C-9), 164.1 (C-5), 167.2 (C-7), 196.3 (C-4); EIMS m/z 272 (M$^+$, 88), 239 (6), 190 (15), 179 (24), 153 (100), 120 (50).

Broussonin A (18). Yellow powder; mp 95–96° C.; UV (MeOH) $\lambda_{max}$ (log ε) 279 (3.67), 231 (3.82) nm; IR (NaCl) $\gamma_{max}$ 3380, 1625, 1558, 1507 cm$^{-1}$; $^1$H NMR (CD$_3$OD, 500 MHz) δ 1.78 (2H, m, H-2), 2.51 (4H, m, H-1 and H-3), 3.71 (3H, s, OCH$_3$), 6.31 (1H, dd, J=2.5 and 8.1 Hz, H-5'), 6.33 (1H, d, J=2.4 Hz, H-3'), 6.67 (2H, d, J=8.6 Hz, H-3''), 6.90 (1H, d, J=8.2 Hz, H-6'), 6.98 (2H, d, J=8.5 Hz, H-2''); $^{13}$C NMR (CD$_3$OD, 125 MHz) δ 30.3 (C-1), 33.5 (C-2), 35.9 (C-3), 55.6 (OCH$_3$), 102.3 (C-3'), 105.4 (C-5'), 116.0 (C-3''), 122.5 (C-1'), 130.3 (C-2''), 131.4 (C-6'), 134.9 (C-1''), 156.2 (C-4''), 157.0 (C-2'), 160.3 (C-4'); EIMS m/z 258 (M$^+$, 62), 151 (21), 137 (100), 107 (26).

2,4,2',4'-Tetrahydroxy-3'-prenylchalcone (19). Yellow needles; mp 150–151° C.; UV (MeOH) $\lambda_{max}$ (log ε) 387 (4.32), 315 (3.90), 259 (3.80), 206.5 (4.40) nm; IR (NaCl) $\gamma_{max}$ 3312, 1616, 1558 cm$^{-1}$; $^1$H NMR (CD$_3$OD, 500 MHz) δ 1.65 (3H, s, H-5''), 1.77 (3H, s, H-4''), 3.32 (2H, brd, H-1''), 5.24 (1H, m, H-2''), 6.34 (1H, s, H-3), 6.35 (1H, overlapped, H-5), 6.39 (1H, d, J=8.9 Hz, H-5'), 7.49 (1H, d, J=8.3 Hz, H-6), 7.69 (1H, d, J=15.4 Hz, H-o), 7.73 (H, d, J=9.0 Hz, H-6'), 8.07 (1H, d, J=15.4 Hz, H-1); $^{13}$C NMR (CD$_3$OD, 125 MHz) δ 16.5 (C-4''), 21.1 (C-1''), 24.6 (C-5'), 102.2 (C-3), 106.7 (C-5'), 107.7 (C-5), 113.3 (C-1'), 114.3 (C-1), 115.1 (C-3'), 116.5 (C-α), 122.2 (C-2''), 128.8 (C-6'), 130.4 (C-3''), 130.9 (C-6), 140.4 (C-β), 159.4 (C-2), 161.4 (C-4), 162.0 (C-4'), 163.7 (C-2'), 193.0 (CO); EIMS m/z 340 (M$^+$, 42), 322 (39), 279 (100), 267 (79), 239 (32), 161 (67), 149 (92).

Moracin N (20). Needles; mp 183–184° C.; UV (MeOH) $\lambda_{max}$ (log ε) 330.5 (4.43), 319.5 (4.49), 218 (4.49) nm; IR (NaCl) $\gamma_{max}$ 3356, 2924, 1617, 1456 cm$^{-1}$; $^1$H NMR (CD$_3$OD, 500 MHz) δ 1.72 (3H, s, H-4''), 1.74 (3H, s, H-5''), 3.32 (2H, brd, H-1''), 5.35 (1H, m, H-2''), 6.23 (1H, t, J=2.2 Hz, H-4'), 6.74 (2H, d, J=2.2 Hz, H-2'), 6.84 (1H, s, H-3), 6.87 (1H, s, H-7), 7.18 (1H, s, H-4); $^{13}$C NMR (CD$_3$OD, 125 MHz) δ 17.8 (C-4''), 26.0 (C-5''), 29.5 (C-1''), 97.8 (C-7), 102.2 (C-3), 103.3 (C-4'), 103.8 (C-2'), 121.4 (C-4), 122.7 (C-9), 124.4 (C-2''), 126.2 (C-5), 132.8 (C-3''), 134.0 (C-1'), 154.6 (C-6), 155.5 (C-2), 155.7 (C-8), 159.9 (C-3'); EIMS m/z 310 (M$^+$, 76), 255 (100), 254 (56), 226 (10).

Albanol A (21). Brown powder; $[\alpha]_D^{20}$ +459.1° (c 0.11, MeOH); UV (MeOH) $\lambda_{max}$ (log ε) 333 (4.30), 319 (4.37), 283 (4.10), 210 (4.51) nm; IR (NaCl) $\gamma_{max}$ 3349, 2910, 1621, 1451, 1256, 1144 cm$^{-1}$; $^1$H NMR (CD$_3$COCD$_3$, 500 MHz) δ 1.77 (3H, s, H-7''), 2.04 (overlap, H-6''), 2.71 (1H, dd, J 5.4 and 17.0 Hz, H-6''), 2.99 (1H, dt, J=5.3 and 11.3 Hz, H-4''), 3.35 (1H, dd, J=5.4 and 11.9 Hz, H-5''), 3.49 (1H, m, H-3''), 6.21 (1H, dd, J=2.4 and 8.6 Hz, H-13''), 6.36 (1H, d, J=2.5 Hz, H-17''), 6.41 (1H, d, J=2.5 Hz, H-11''), 6.45 (1H, brd, J=5.6 Hz, H-2''), 6.49 (1H, dd, J=2.5 and 8.3 Hz, H-19''), 6.80 (1H, dd, J=2.0 and 8.4 Hz, H-5), 6.94 (1H, d, J=1.6 Hz, H-6), 6.97 (2H, s, H-7 and H-2), 7.03 (1H, s, H-3), 7.13 (1H, d, J=8.4 Hz, H-20''), 7.23 (1H, d, J=8.6 Hz, H-14''), 7.39 (1H, d, J=8.3 Hz, H-4); MALDIMS m/z 562 [M]+; FABMS m/z 561 [M−H]$^-$, 459 (23), 352 (15), 306 (95), 199 (85), 168 (88), 153 (100), 122 (35).

(2S)-2',4'-Dihydroxy-7-methoxy-8-prenylflavan (22). Brown powder; mp 95–96° C.; $[\alpha]_D^{20}$ −5.2° (c 0.25, MeOH); UV (MeOH) $\lambda_{max}$ (log ε) 280 (3.46), 208 (4.52) nm; CD (MeOH) nm $\Delta\epsilon_{277.9}$−8.0; IR (NaCl) $\gamma_{max}$ 3392, 2920, 1615, 1488 cm$^{-1}$; $^1$H and $^{13}$C NMR data, see Table 2; EIMS m/z 340 (M$^+$, 100), 284 (20), 205 (43), 189 (42), 161 (57), 149 (86); HREIMS m/z 340.1668, calcd for C$_{21}$H$_{24}$O$_4$, 340.1674.

(2S)-7,4'-Dihydroxyflavan. Brown powder; mp 110–111° C.; $[\alpha]_D^{20}$ −55.0° (c 0.02, MeOH); UV (MeOH) $\lambda_{max}$ (log ε) 282 (3.25), 223 (3.84), 204 (4.38) nm; CD (MeOH) nm $\Delta\epsilon_{276.5}$ −11.0; IR (NaCl) $\gamma_{max}$ 3348, 2927, 1507, 1456 cm$^{-1}$; $^1$H NMR (CD$_3$OD, 300 MHz) δ 1.99 (1H, m, H-3), 2.09 (1H, m, H-3), 2.67 (1H, m, H-4), 2.86 (1H, m, H-4), 4.91 (1H, overlapped, H-2), 6.24 (1H, d, J=2.4 Hz, H-8), 6.30 (1H, dd, J=2.4 and 8.2 Hz, H-6), 6.77 (2H, d, J=8.6 Hz, H-3'), 6.85 (1H, d, J=8.2 Hz, H-5), 7.22 (2H, d, J=8.6 Hz, H-2') EIMS m/z 242 (M$^+$, 100), 149 (18), 136 (23), 123 (62) 120 (89).

(2R,3R)-Lespedezaflavanone C. Yellow powder; mp 95–96° C.; $[\alpha]_D^{20}$ −45.0° (c 0.02, MeOH); UV (MeOH) $\lambda_{max}$ (log ε) 296 (4.17), 204 (4.92) nm; CD (MeOH) nm $\Delta\epsilon_{294.4}$ −178.8; IR (NaCl) $\gamma_{max}$ 3420, 2927, 1635, 1558, 1456 cm$^{-1}$; $^1$H NMR (CD$_3$OD, 500 MHz) δ 1.47 (3H, s, H-4''), 1.60 (3H, s, H-5''), 1.72 (3H, s, H-4''), 1.73 (3H, s, H-5'''), 3.12 (1H, brd, J=7.5 Hz, H-1''), 3.32 (1H, brd, H-1'''), 4.48 (1H, d, J=11.4 Hz, H-3), 4.90 (1H, d, J=11.4 Hz, H-2), 5.12 (1H, m, H-2''), 5.34 (1H, m, H-2'''), 5.96 (1H, s, H-6) 6.79 (1H, d, J=8.1 Hz, H-5'), 7.16 (1H, dd, J=2.2 and 8.2 Hz, H-6'), 7.22 (1H, d, J=2.1 Hz, H-2'); $^{13}$C NMR (CD$_3$OD, 125 MHz) δ 17.9 (C-4'' and C-4'''), 22.3 (C-1''), 25.98 (C-5''), 25.99 (C-5'''), 29.3 (C-1'''), 73.7 (C-3), 85.1 (C-2), 96.7 (C-6), 101.9 (C-10), 109.2 (C-8), 115.5 (C-5'), 123.7 (C-2''), 123.9 (C-2'''), 127.5 (C-6'), 128.4 (C-3'), 129.3 (C-1'), 130.2 (C-2'), 131.7 (C-3''), 133.1 (C-3'''), 156.8 (C-4'), 161.3 (C-9), 163.0 (C-5), 166.4 (C-7), 198.8 (C-4); EIMS m/z 424 (M$^+$, 24), 256 (21), 221 (44), 202 (97), 175 (41), 165 (100), 149 (64), 137 (73).

Bavachin. Colorless needles; $[α]_D^{20}$ −50.0 (c 0.02, MeOH); UV (MeOH) λ$_{max}$ (log ε) 276 (3.32), 236 (3.53), 206 (3.74) nm; IR (NaCl) λ$_{max}$ 1706, 1652, 1558, 1507 cm$^{-1}$; $^1$H NMR (CD$_3$OD, 500 MHz) δ 1.70 (3H, s, H-4''), 1.75 (3H, s, H-5''), 2.65 (1H, dd, J=2.9 and 16.8 Hz, H-3), 3.02 (1H, dd, J=13.1 and 16.8 Hz, H-3), 3.21 (1H, d, J=7.6 Hz, H-1''), 5.30 (1H, m, H-2''), 5.34 (1H, dd, J=2.7 and 12.7 Hz, H-2), 6.33 (1H, s, H-8), 6.80 (2H, d, J=8.6 Hz, H-3'), 7.31 (2H, d, J=8.5 Hz, H-2'), 7.55 (1H, s, H-5); $^{13}$C NMR (CD$_3$OD, 125 MHz) δ 17.8 (C-4''), 26.0 (C-5''), 28.4 (C-2''), 45.1 (C-3), 81.1 (C-2), 103.2 (C-8), 113.7 (C-10), 116.3 (C-3'), 123.3 (C-2''), 124.7 (C-6), 128.3 (C-5), 129.0 (C-2'), 131.5 (C-1'), 133.4 (C-3''), 159.0 (C-4'), 163.4 (C-9), 164.9 (C-7), 193.7 (C-4); EIMS m/z 324 (M$^+$, 100), 205 (81), 189 (22), 149 (63), 120 (42).

(2R,3R)-Katuranin. Needles; mp 239–240° C.; $[α]_D^{20}$+ 28.60 (c 0.07, MeOH); UV (MeOH) λ$_{max}$ (log ε) 291 (4.16), 215.5 (4.33) nm; CD (MeOH) nm Δε$_{290}$ −43.2; IR (NaCl) γ$_{max}$ 3243, 1635, 1507 cm$^{-1}$; $^1$H NMR (CD$_3$COCD$_3$, 500 MHz) δ 4.64 (1H, d, J=11.6 Hz, H-3), 5.06 (1H, d, J=11.6 Hz, H-2), 5.93 (1H, d, J=2.1 Hz, H-8), 5.98 (1H, d, J=2.1 Hz, H-6), 6.88 (2H, d, J=8.2 Hz, H-3'), 7.40 (2H, d, J=8.2 Hz, H-2'); $^{13}$C NMR (CD$_3$COCD$_3$, 125 MHz) δ 72.2 (C-3), 83.5 (C-2), 95.2 (C-8), 96.2 (C-6), 100.6 (C-10), 115.0 (C-3'), 128.2 (C-1'), 129.4 (C-2'),157.9 (C-4'), 163.3 (C-9), 164.1 (C-5), 167.0 (C-7), 197.4 (C-4); EIMS m/z 288 (M$^+$, 41), 259 (54), 165 (20), 153 (100) 134 (41).

Gancaonin P. Yellow powder; UV (MeOH) λ$_{max}$ (log ε) 261 (4.13), 205 (4.79) nm; $^1$H NMR (CD$_3$COCD$_3$, 500 MHz) δ 1.66 (3H, s, H-5'), 1.82 (3H, s, H-4'), 3.56 (2H, d, J=6.0 Hz, H-1'), 5.29 (1H, m, H-2'), 6.36 (1H, s, H-8), 7.00 (1H, d, J=8.3 Hz, H-5'), 7.72 (1H, brd, J=7.4 Hz, H-6'), 7.87 (1H, s, H-2'); EIMS m/z 370 (M$^+$, 100), 355 (94), 315 (45), 302 (37), 244 (12), 137 (21).

(2R,3R)-5,7,2',4'-Tetrahydroxyflavanonol. Yellow powder; $[α]_D^{20}$ +10.30 (c 0.35, MeOH); UV (MeOH) λ$_{max}$ (log ε) 289 (3.85), 225 (3.94), 208 (4.12) nm; CD (MeOH) nm Δε$_{295}$-44.8; IR (NaCl) γ$_{max}$ 3257, 2938, 1641, 1468, 1272, 1160 cm$^{-1}$; $^1$H NMR (CD$_3$COCD$_3$, 500 MHz) δ 4.86 (1H, d, J=11.5 Hz, H-3), 5.48 (1H, d, J=11.5 Hz, H-2), 5.92 (1H, s, H-8), 5.98 (1H, s, H-6), 6.42 (1H, d, J=8.3 Hz, H-5'), 6.45 (1H, s, H-3'), 7.30 (1H, d, J=8.3 Hz, H-6'); EIMS m/z 304 (M$^+$, 29), 275 (36), 153 (100), 149 (32) 123 (59).

Broussonin B. Colorless needles; mp 88–89° C.; UV (MeOH) λ$_{max}$ (log ε) 266 (3.11), 239 (3.10) nm; IR (NaCl) γ$_{max}$ 3335, 2954, 1614, 1508, 1456 cm$^{-1}$; $^1$H NMR (CD$_3$OD, 300 MHz) δ 1.76 (2H, m, H-2), 2.49 (4H, m, H-1 and H-3), 3.74 (3H, s, OCH$_3$), 6.29 (1H, dd, J=2.4 and 8.1 Hz, H-5'), 6.38 (1H, d, J=2.4 Hz, H-3'), 6.68 (2H, d, J=8.5 Hz, H-3''), 6.86 (1H, d, J=8.1 Hz, H-6'), 6.98 (2H, d, J=8.5 Hz, H-2''); $^{13}$C NMR (CD$_3$OD, 75 MHz) δ 30.3 (C-1), 33.5 (C-2), 35.8 (C-3), 55.6 (OCH$^3$), 99.7 (C-3'), 107.5 (C-5'), 116.0 (C-3''), 122.8 (C-1'), 130.3 (C-2''), 131.1 (C-6'), 134.8 (C-1''), 156.1 (C-4''), 157.6 (C-4'), 159.6 (C-2'); EIMS m/z 258 (M$^+$, 52), 151 (18), 137 (100), 134 (20), 107 (48).

Broussonin E.* $^1$H NMR (CD$_3$OD, 500 MHz) d 1.80 (2H, m, H-2), 2.50 (4H, m, H-1 and H-3), 3.71 (3H, s, OCH$_3$-4'), 3.80 (3H, s, OCH$_3$-4''), 6.31 (1H, dd, J=2.5 and 8.2 Hz, H-5'), 6.33 (1H, d, J=2.4 Hz, H-3'), 6.58 (overlap, H-6''), 6.64 (1H, d, J=2.1 Hz, H-2''), 6.79 (1H, d, J=8.2 Hz, H-5''), 6.91 (1H, d, J=8.2 Hz, H-6'); $^{13}$C NMR (CD$_3$OD, 125 MHz) δ 30.3 (C-1), 33.3 (C-2), 36.1 (C-3), 55.5 (OCH$^3$-4'), 56.5 (OCH$_3$-4''), 102.3 (C-5'), 105.4 (C-3'), 112.8 (C-5''), 116.5 (C-2''), 120.5 (C-6''), 122.4 (C-1'), 131.4 (C-6'), 137.1 (C-1''), 147.0 (C-4''), 147.3 (C-3''), 157.1 (C-2'), 160.3 (C-4').

*Isolated as a mixture of broussonins E and F.

Broussonin F.* $^1$H NMR (CD$_3$OD, 500 MHz) δ 1.80 (2H, m, H-2), 2.50 (4H, m, H-1 and H-3), 3.75 (3H, s, OCH$_3$-2'), 3.81 (3H, s, OCH$_3$-3''), 6.28 (1H, dd, J=2.3 and 8.1 Hz, H-5'), 6.37 (1H, d, J=2.3 Hz, H-3'), 6.60 (overlap, H-6''), 6.68 (1H, d, J=7.9 Hz, H-5''), 6.71 (1H, d, J=1.7 Hz, H-2''), 6.86 (1H, d, J=8.1 Hz, H-6'); $^{13}$C NMR (CD$_3$OD, 125 MHz) δ 30.3 (C-1), 33.5 (C-2), 36.3 (C-3), 55.6 (OCH$^3$-2'), 56.3 (OCH$^3$-3''), 99.7 (C-3'), 107.5 (C-5'), 113.1 (C-2''), 116.0 (C-5''), 121.8 (C-6''), 122.8 (C-1'), 131.2 (C-6'), 135.1 (C-1''), 146.0 (C-4''), 148.7 (C-3''), 157.7 (C-4'), 159.1 (C-2').

*Isolated as a mixture of broussonins E and F.

Broussochalcone A. Orange powder; UV (MeOH) λ$_{max}$ (log ε) 277 (3.59), 206 (4.16) nm; IR (NaCl) γ$_{max}$ 3389, 2924, 2854, 1594, 1272 cm$^{-1}$; $^1$H NMR (CD$_3$COCD$_3$, 500 MHz) δ 1.72 (3H, s, H-4''), 1.74 (3H, s, H-5''), 5.34 (1H, m, H-2''), 6.39 (1H, s, H-3'), 6.88 (1H, d, J=7.9 Hz, H-5), 7.16 (1H, brd, J=7.6 Hz, H-6), 7.30 (1H, brs, H-2), 7.65 (1H, d, J=15.3 Hz, H-a), 7.74 (1H, d, J=15.3 Hz, H-i), 7.94 (1H, s, H-6'); ESMS m/z 339 [M–H]$^-$.

Broussochalcone B. Yellow powder; mp 157–158° C.; UV (MeOH) λ$_{max}$ (log ε) 373 (4.23), 205 (4.43) nm; IR (NaCl) γ$_{max}$ 3350, 2923, 1645, 1558, 1508 cm$^{-1}$; $^1$H NMR (CD$_3$OD, 500 MHz) δ 1.75 (3H, s, H-4''), 1.76 (3H, s, H-5''), 3.27 (2H, d, J=7.2 Hz, H-1''), 5.34 (1H, m, H-2''), 6.29 (1H, s, H-3'), 6.85 (2H, d, J=8.5 Hz, H-3), 7.54 (1H, d, J=15.4 Hz, H-a), 7.59 (2H, d, J=8.5 Hz, H-2), 7.72 (1H, s, H-6'), 7.76 (1H, d, J=15.3 Hz, H-β); $^{13}$C NMR (CD$_3$OD, 125 MHz) δ 17.8 (C-4''), 26.0 (C-5''), 28.9 (C-1''), 103.4 (C-3'), 114.4 (C-1'), 117.0 (C-3), 118.6 (C-o), 122.2 (C-5'), 124.2 (C-2''), 127.4 (C-1), 131.9 (C-2), 132.4 (C-6'), 133.1 (C-3''), 145.4 (C-β), 161.5 (C-4), 164.6 (C-4'), 165.5 (C-2'), 193.4 (CO); EIMS m/z 324 (M$^+$, 100), 231 (10), 205 (77), 147 (12).

Isobavachalcone. Yellow powder; mp 75–76° C.; UV (MeOH) λ$_{max}$ (log ε) 368 (4.09), 206 (4.08) nm; IR (NaCl) γ$_{max}$ 3395, 2921, 1635 cm$^{-1}$; $^1$H NMR (CD$_3$OD, 500 MHz) δ 1.63 (3H, s, H-5''), 1.77 (3H, s, H-4''), 3.34 (2H, d, J=7.2 Hz, H-1''), 5.26 (1H, m, H-2''), 6.53 (1H, d, J=8.8 Hz, H-5'), 6.92 (2H, d, J=8.5 Hz, H-3), 7.72 (2H, d, J=8.4 Hz, H-2), 7.74 (1H, d, J=15.2 Hz, H-1), 7.82 (1H, d, J=15.3 Hz, H-β), 7.96 (H, d, J=8.9 Hz, H-6'); $^{13}$C NMR (CD$_3$OD, 125 MHz) δ 17.9 (C-4''), 22.2 (C-1''), 25.8 (C-5''), 107.9 (C-5'), 114.4 (C-1'), 116.0 (C-3'), 116.7 (C-3), 118.5 (C-α), 123.2 (C-2''), 127.6 (C-1), 130.3 (C-6'), 131.5 (C-3''), 131.7 (C-2), 144.9 (C-β), 160.9 (C-4), 162.6 (C-4'), 164.7 (C-2'), 192.5 (CO); EIMS m/z 324 (M$^+$, 100), 281 (83), 269 (22), 176 (22) 161 (36), 149 (96), 120 (31).

2,4,2',4'-Tetrahydroxychalcone. Orange powder; UV (MeOH) λ$_{max}$ (log ε) 387 (3.34), 204 (4.12) nm; IR (NaCl) γ$_{max}$ 3283, 1599, 1228, 839 cm$^{-1}$; $^1$H NMR (CD$_3$COCD$_3$, 500 MHz) δ 6.35 (1H, d, J=2.3 Hz, H-3'), 6.45 (2H, dd, J=2.2 and 8.2 Hz, H-5 and H-5'), 6.53 (1H, d, J=2.3 Hz, H-3), 7.69 (1H, d, J=8.6 Hz, H-6), 7.79 (1H, d, J=15.4 Hz, H-α), 8.02 (1H, d, J=8.9 Hz, H-6'), 8.21 (1H, d, J=15.4 Hz, H-β); ESMS m/z 271 [M–H]$^-$.

Moracin D. Dark brown powder; mp>250° C.; UV (MeOH) $\lambda_{max}$ (log ϵ) 335 (4.16), 322 (4.15), 216 (4.29) nm; IR (NaCl) $\gamma_{max}$ 3348, 2927, 1681, 1558 cm⁻; ¹H NMR (Me₂CO-d₆, 500 MHz) δ 1.42 (6H, s, H-4" and H-5"), 5.68 (1H, d, J=9.9 Hz, H-2"), 6.70 (1H, d, J=9.8 Hz, H-1"), 6.78 (1H, brs, H-6'), 6.81 (1H, dd, J=1.9 and 8.2 Hz, H—S), 6.94 (1H, d, J=1.6 Hz, H-2'), 6.97 (1H, brs, H-7), 7.05 (1H, s, H-3), 7.40 (1H, d, J=8.5 Hz, H-4); ¹³C NMR (Me₂CO-d₆, 125 MHz) δ 28.0 (C-4" and C—S"), 76.5 (C-3"), 98.3 (C-7), 102.4 (C-3), 104.3 (C-2'), 104.7 (C-6'), 109.6 (C-4'), 113.2 (C-5), 117.6 (C-1"), 122.0 (C-4), 122.5 (C-9), 129.6 (C-2"), 132.0 (C-1'), 154.2 (C-2), 155.2 (C-6, C-3', and C-5'), 156.7 (C-8); EIMS m/z 308 (M⁺, 26), 293 (100), 146 (15).

Moracin I. Brown powder; mp 93–94° C.; UV (MeOH) $\lambda_{max}$ (log ϵ) 309 (4.32), 226 (4.40) nm; IR (NaCl) $\gamma_{max}$ 3364, 2927, 1622, 1597 cm⁻¹; ¹H NMR (CD₃OD, 500 MHz) δ 1.65 (6H, s, H-4" and H—S"), 3.42 (2H, d, J=6.2 Hz, H-1"), 3.80 (3H, S, OCH₃), 5.11 (1H, m, H-2"), 6.46 (1H, d, J=2.2 Hz, H-4'), 6.69 (1H, s, H-3), 6.71 (1H, d, J=2.3 Hz, H-2'), 6.74 (1H, dd, J=2.0 and 8.2 Hz, H-5), 6.91 (1H, d, J=1.6 Hz, H-7), 7.35 (1H, d, J=8.3 Hz, H-4); ¹³C NMR (CD₃OD, 125 MHz) δ 18.1 (C-4"), 25.9 (C-5"), 26.6 (C-1"), 56.1 (OCH₃), 98.4 (C-7), 100.2 (C-4'), 105.9 (C-3) 108.1 (C-2'), 113.1 (C-5), 120.6 (C-1'), 122.0 (C-4), 122.9 (C-9), 125.5 (C-2"), 131.5 (C-3"), 132.8 (C-6'), 155.8 (C-2), 156.7 (C-8), 157.1 (C-6), 157.3 (C-3'), 160.4 (C-5'); EIMS m/z 324 (M⁺, 100), 309 (34), 281 (44), 202 (60), 163 (13).

Moracin M. Needles; UV (MeOH) $\lambda_{max}$ (log ϵ) 328 (4.36), 315 (4.44), 215 (4.45) nm; IR (NaCl) $\gamma_{max}$ 3339, 1612, 1442, 1292, 1151, 1000 cm⁻¹; ¹H NMR (CD₃OD, 500 MHz) δ 6.25 (1H, t, J=2.2 Hz, H-4'), 6.73 (1H, dd, J=2.2, 8.4 Hz, H-5), 6.76 (2H, d, J=2.2 Hz, H-2' and 6'), 6.90 (1H, d, J=1.8 Hz, H-7), 6.91 (1H, s, H-3), 7.34 (1H, d, J=8.3 Hz, H-4); ¹³C NMR (CD₃OD, 125 MHz) δ 98.4 (C-7), 102.2 (C-3), 103.5 (C-4'), 103.9 (C-2' and C-6'), 113.2 (C-5), 122.0 (C-4), 123.0 (C-9), 133.8 (C-1'), 156.1 (C-6), 156.8 (C-2), 157.2 (C-8), 159.9 (C-3'); EIMS m/z 242 (M⁺, 100), 213 (9), 121 (10).

(3S,5R)-Loliolide. Colorless prisms; mp 148–149° C.; $[\alpha]_D^{20}$ −91.3° (c 0.05, MeOH); UV (MeOH) $\lambda_{max}$ (log ϵ) 228 (3.55) nm; IR (NaCl) $\gamma_{max}$ 3433, 2924, 1731, 1651 cm⁻¹; ¹H NMR (CD₃OD, 500 MHz) δ 1.26 (3H, s, H-10), 1.46 (3H, s, H-11), 1.52 (1H, dd, J=3.6 and 14.4 Hz, H-2), 1.72 (1H, overlapped, H-4), 1.75 (3H, s, H-9), 1.98 (1H, dt, J=2.5 and 13.7 Hz, H-2), 2.41 (1H, dt, J=2.5 and 13.7 Hz, H-4), 4.21 (1H, m, H-3), 5.74 (1H, s, H-7); ¹³C NMR (CD₃OD, 125 MHz) δ 27.0 (C-11), 27.5 (C-9), 31.0 (C-10), 37.2 (C-1), 46.5 (C-4), 48.0 (C-2), 67.3 (C-3), 88.9 (C-5), 113.4 (C-7), 174.5 (C-8), 185.7 (C-6); CIMS (methane) m/z 197 (M+H+, 100).

Marmesin. Colorless needles; mp 186–187° C.; $[\alpha]_D^{20}$ −28.3° (c 0.05, MeOH); UV (MeOH) $\lambda_{max}$ (log ϵ) 334 (4.22), 258 (3.55), 248 (3.63), 224 (4.05), 210 (4.10) nm; IR (NaCl) $\gamma_{max}$ 3489, 2971, 1707, 1629 cm⁻¹; ¹H NMR (CDCl₃, 300 MHz) δ 1.24 (3H, s, H-4'), 1.37 (3H, s, H-5'), 3.21 (2H, m, H-1'), 4.74 (1H, t, J=9.1 Hz, H-2'), 6.20 (1H, d, J=9.4 Hz, H-3), 6.72 (1H, s, H-8), 7.22 (1H, s, H-5), 7.58 (1H, d, J=9.5 Hz, H-4); ¹³C NMR (CDCl₃, 75 MHz) d 24.3 (C-4'), 26.1 (C-5'), 29.5 (C-1'), 71.6 (C-3'), 91.1 (C-2'), 97.9 (C-8), 112.2 (C-3), 112.8 (C-10), 123.4 (C-5), 125.1 (C-6), 143.7 (C-4), 155.6 (C-9), 161.5 (C-2), 163.2 (C-7); EIMS m/z 246 (M⁺, 46), 187 (100).

trans-Resveratrol. Needles; mp 256–257° C.; UV (MeOH) $\lambda_{max}$ (log ϵ) 306 (4.48), 217 (4.36) nm; IR $\lambda_{max}$ (neat) 3287, 2916, 1586, 1511, 1152 cm⁻¹; ¹H NMR (CD₃COCD₃, 300 MHz) δ 6.28 (1H, t, J=2.1 Hz, H-4), 6.54 (2H, d, J=2.1 Hz, H-2), 6.84 (2H, d, J=8.4 Hz, H-2'), 6.89 (1H, d, J=16.4 Hz, H-α), 7.03 (1H, d, J=16.4 Hz, H-i), 7.43 (2H, d, J=8.4 Hz, H-3'); ¹³C NMR (CD₃COCD₃, 75 MHz) δ 102.6 (C-4), 105.7 (C-2), 116.4 (C-3'), 126.8 (C-1), 128.7 (C-2'), 129.1 (C-β), 129.9 (C-1'), 140.8 (C-1), 158.1 (C-4'), 159.5 (C-3); ESMS m/z 227 [M−H]⁻.

5,7-Dihydroxycoumarin. Needles; mp 274–275° C.; UV (MeOH) $\lambda_{max}$ (log ϵ) 329 (3.64), 258 (3.49), 207 (4.10) nm; IR (NaCl) $\gamma_{max}$ 3244, 1683, 1616 cm⁻¹; ¹H NMR (CD₃OD, 500 MHz) δ 6.02 (1H, d, J=9.5 Hz, H-3), 6.20 (1H, d, J=1.9 Hz, H-8), 6.21 (1H, d, J=2.0 Hz, H-6), 8.05 (1H, d, J=9.6 Hz, H-4), (DMSO-d₆, 500 MHz) δ 5.99 (1H, d, J=9.6 Hz, H-3), 6.15 (1H, d, J=1.7 Hz, H-8), 6.24 (1H, d, J=2.0 Hz, H-6), 7.94 (1H, d, J=9.6 Hz, H-4); ¹³C NMR (CD₃OD, 125 MHz) δ 95.3 (C-8), 99.4 (C-6), 103.7 (C-10), 109.3 (C-3), 141.6 (C-4), 157.7 (C-5), 158.1 (C-9), 164.0 (C-7), 164.4 (C-2), (DMSO-d₆, 125 MHz) δ 94.1 (C-8), 98.4 (C-6), 101.8 (C-10), 108.7 (C-3), 139.8 (C-4), 156.3 (C-9), 156.7 (C-5), 161.0 (C-2), 162.3 (C-7); EIMS m/z 178 (M⁺, 100), 150 (96).

TABLE 1

¹H and ¹³C NMR Data of Compounds 1–3 in Acetone-d₆[a]

| Carbon | δ$_H$ | | | δ$_c$ | | |
|---|---|---|---|---|---|---|
| | 1 | 2 | 3 | 1 | 2 | 3 |
| 2 | | | | 162.4 | 146.6 | 156.6 |
| 3 | | | | 121.8 | 136.6 | 139.5 |
| 4 | | | | 183.0 | 176.5 | 180.2 |
| 5 | | | | 163.4 | 158.9 | 160.0 |
| 6 | 6.25, brs | | | 99.2 | 111.7 | 111.3 |
| 7 | | | | 164.7 | 162.7 | 162.3 |
| 8 | 6.33, brs | 6.59, brs | 6.57, s | 94.2 | 93.8 | 94.0 |
| 9 | | | | 159.3 | 155.6 | 155.3 |
| 10 | | | | 105.3 | 104.0 | 105.7 |
| 1' | | | | 113.0 | 123.8 | 123.1 |
| 2' | | 7.81, brs | 7.69, d (1.8) | 157.2 | 115.6 | 116.5 |
| 3' | 6.57, brs | | | 103.8 | 145.7 | 146.1 |
| 4' | | | | 161.4 | 148.2 | 149.1 |
| 5' | 6.51, brd (8.3) | 6.99, d (8.6) | 6.99, d (8.4) | 108.0 | 116.2 | 116.4 |
| 6' | 7.19, d (8.3) | 7.68, d (7.9) | 7.56, dd (2.0, 8.3) | 132.3 | 121.3 | 122.2 |
| 1" | 3.12, d (6.9) | 3.37, d (7.1) | 3.37, d (7.1) | 24.4 | 21.9 | 21.9 |
| 2" | 5.14, m | 5.29, brt (6.8) | 5.30, m | 122.6 | 123.1 | 123.3 |
| 3" | | | | 135.8 | 135.3 | 135.7 |
| 4" | 1.89, m | 1.96, m | 1.95, m | 40.4 | 40.5 | 40.6 |
| 5" | 1.43, s | 1.79, S | 1.80, s | 16.0 | 16.2 | 16.2 |
| 6" | 2.00, m | 2.05, m | 2.05, m | 27.3 | 27.3 | 27.5 |
| 7" | 5.04, m | 5.07, m | 5.08, m | 125.1 | 125.1 | 125.4 |
| 8" | | | | 131.6 | 131.6 | 131.7 |
| 9" | 1.61, s | 1.54, s | 1.56, s | 25.8 | 17.6 | 17.7 |
| 10" | 1.55, s | 1.59, s | 1.61, s | 17.7 | 28.8 | 25.9 |
| —OCH³ | | | 3.86, s | | | 60.2 |

[a]TMS was used as the internal standard; chemical shifts are shown in the d scale with J values (Hz) in parentheses.

TABLE 2

¹H and ¹³C NMR Data of Compounds 4, 22, and 11[a]

| Carbon | δ$_H$ | | | δ$_c$ | | |
|---|---|---|---|---|---|---|
| | 4[b] | 22[b] | 11[c] | 4[b] | 22[b] | 11[c,d] |
| 2 | 4.83, dd (2.2, 9.6) | 5.23, dd (1.7, 9.8) | 5.75, m | 79.1 | 74.3 | 76.1 |
| 3 | 1.93, m 2.04, m | 1.84, m 2.14, m | 2.70, m 3.03, m | 31.2 | 29.9 | 44.1 |

TABLE 2-continued

¹H and ¹³C NMR Data of Compounds 4, 22, and 11[a]

| Carbon | δ_H 4[b] | δ_H 22[b] | δ_H 11[c] | δ_c 4[b] | δ_c 22[b] | δ_c 11[c,d] |
|---|---|---|---|---|---|---|
| 4 | 2.62, m<br>2.80, m | 2.62, m<br>2.83, m | | 25.4 | 25.9 | 191.1 |
| 5 | 6.83, d<br>(8.2) | 6.80, d<br>(8.4) | 7.70, d<br>(8.4) | 131.0 | 127.8 | 129.4 |
| 6 | 6.30, dd<br>(2.4, 8.2) | 6.41, d<br>(8.4) | 6.48<br>(overlap) | 109.0 | 104.1 | 104.8 |
| 7 | | | | 157.5 | 157.6 | 167.9 |
| 8 | 6.24, d<br>(2.3) | | | 104.0 | 118.3 | 115.0 |
| 9 | | | | 157.2 | 154.8 | 160.0 |
| 10 | | | | 114.3 | 116.0 | e |
| 1' | | | | 134.0 | 121.4 | 117.9 |
| 2' | 7.06, d<br>(1.8) | | | 128.5 | 156.1 | 156.2 |
| 3' | | 6.34, d<br>(2.1) | 6.48<br>(overlap) | 129.1 | 103.3 | 103.5 |
| 4' | | | | 155.8 | 158.5 | 159.6 |
| 5' | 6.73, d<br>(8.1) | 6.31, dd<br>(2.0, 8.3) | 6.44, brd<br>(8.4) | 115.6 | 107.4 | 108.0 |
| 6' | 7.01, dd<br>(2.0, 8.2) | 7.15, d<br>(8.3) | 7.36, d<br>(8.4) | 125.6 | 128.3 | 129.0 |
| 1" | 3.28, d<br>(7.3) | | 3.09, m | 29.8 | 23.1 | 28.0 |
| 2" | 5.30, m | 5.14, brt<br>(7.0) | 4.78, dt<br>(2.2, 8.1) | 123.9 | 124.6 | 92.0 |
| 3" | | | | 133.0 | 131.1 | 71.4 |
| 4" | 1.68, s | 1.64, s | 1.28, 2 | 17.8 | 18.0 | 25.7 |
| 5" | 1.71, s | 1.61, s | 1.21, s | 26.0 | 26.0 | 26.1 |
| —OCH₃ | | 3.70, s | | | | 56.1 |

[a]TMS was used as the internal standard, chemical shifts are shown in the d scale with J values (Hz) in parentheses.
[b]Me OH-d₄.
[c]Acetone-d₆.
[d]Signals derived from HMBC experiment.
[e]No signal detected.

TABLE 3

¹H and ¹³C NMR Data of Compounds 5–7 in MeOH-d₄[a]

| Carbon | δ_H 5 | δ_H 6 | δ_H 7 | δ_c 5 | δ_c 6 | δ_c 7 |
|---|---|---|---|---|---|---|
| 1 | 2.51, m | 2.52, m | 2.53, m | 30.3 | 30.8 | 29.2 |
| 2 | 1.79, m | 1.80, m | 1.81, m | 33.6 | 33.1 | 31.8 |
| 3 | 2.51, m | 2.52, m | 2.53, m | 35.9 | 35.9 | 34.8 |
| 1' | | | | 121.3 | 121.8 | 123.1 |
| 2' | | | | 157.0 | 154.3 | 158.2 |
| 3' | 6.26, d<br>(2.4) | | 6.35, brd | 103.4 | 117.2 | 98.7 |
| 4' | | | | 157.2 | 155.1 | 154.8 |
| 5' | 6.20, dd<br>(2.4, 8.1) | 6.27, d<br>(8.2) | 6.31, dd<br>(2.4, 8.1) | 107.2 | 108.1 | 106.3 |
| 6' | 6.81, d<br>(8.1) | 6.68, d<br>(overlap) | 6.93, d<br>(8.1) | 131.4 | 128.0 | 129.9 |
| 1" | | | | 135.0 | 135.0 | 134.9 |
| 2" | 6.98, d<br>(8.6) | 6.98, d<br>(8.4) | 6.89, brs | 130.3 | 130.3 | 130.1 |
| 3" | 6.67, d<br>(8.6) | 6.67, d<br>(overlap) | | 115.9 | 116.0 | 126.2 |
| 4" | | | | 156.1 | 156.3 | 152.0 |
| 5" | 6.67, d<br>(8.6) | 6.67, d<br>(overlap) | 6.69, d<br>(7.8) | 115.9 | 116.0 | 115.5 |
| 6" | 6.98, d<br>(8.6) | 6.98, d<br>(8.4) | 6.91, d<br>(overlap) | 130.3 | 130.3 | 127.2 |
| 1''' | | 3.33, brd<br>(9.6) | 3.30, d<br>(7.0) | | 23.6 | 30.0 |
| 2''' | | 5.21, m | 5.29, m | | 124.7 | 122.0 |
| 3''' | | | | | 131.7 | 134.5 |
| 4''' | | 1.77, s | 1.76, s | | 18.0 | 25.8 |
| 5''' | | 1.66, s | 1.74, s | | 26.0 | 25.8 |
| OCH₃ | | | 3.76, s | | | 55.3 |

[a]TMS was used as the internal standard; chemical shifts are shown in the d scale with J values (Hz) in parentheses.

Assay for Inhibition of Aromatase Activity. Microsomes were prepared from freshly delivered human term placentas using 0.05 M potassium phosphate buffer, pH 7.4, and stored frozen in plastic tubes at −70° C. Reaction mixtures were prepared in glass tubes containing 4 μL of placental microsomes (5 mg/mL), 0.3 μL of [1,2-³H]androstenedione (42.0 Ci/mmol, 1.0 mCi/mL) (NEN Life Science Products, Boston, Mass.), 5 μL of unlabelled androstenedione (0.875 μM), 5 pL of NADPH (0.48 mM), 10 μL of test sample (dissolved in DMSO), and 0.05 M potassium phosphate buffer, pH 7.4 (500 μL, final volume). After a 4 min incubation at 37° C., the reaction was terminated by adding 3 mL of chloroform. The tubes were centrifuged at 2,000×g for 10 min and then 300 μL of the aqueous phases were transferred to tubes containing 300 μL of charcoal/dextrin solution (5%). Following another 10 min centrifugation at 2,000×g, supernatant fractions (500 μL) were used for the determination of radioactivity. Inhibition of aromatase activity was calculated using the following equation:

$$\% \text{ Inhibition} = \left[1 - \frac{\text{Sample }(DPM) - \text{Blank }(DPM)}{\text{DMSO }(DPM) - \text{Blank }(DPM)}\right] \times 100$$

Samples were tested in duplicate and the mean values were used to prepare dose-response curves. Results were typically expressed as $IC_{50}$ values. Aminoglutethimide (Sigma, St. Louis, Mo.) was used as a positive control.[25,26,54,55]

TABLE 4

Aromatase Inhibitory Activity of
Compounds 1, 8–21, and Aminoglutethimide[a]

| Compound | $IC_{50}$ (μM) |
|---|---|
| 1 | 24.0 |
| 8 | 7.1 |
| 9 | 0.5 |
| 10 | 31.1 |
| 11 | 0.1 |
| 12 | 0.1 |
| 13 | 0.4 |
| 14 | 2.2 |
| 15 | 3.4 |
| 16 | 9.7 |
| 17 | 17.0 |
| 18 | 30.0 |
| 19 | 4.6 |

TABLE 4-continued

Aromatase Inhibitory Activity of
Compounds 1, 8–21, and Aminoglutethimide[a]

| Compound | IC$_{50}$ ($\mu$M) |
|---|---|
| 20 | 31.1 |
| 21 | 7.5 |
| Aminoglutethimide | 6.4 |

[a]Compounds 2–7, 22, (2S)-7,4'-dihydroxyflavan, (2R,3R)-lespedezaflavanone C, bavachin, (2R,3R)-katuranin, gancaonin P, (2R,3R)-5,7,2',4'-tetrahydroxyflavanonol, broussonins B, E, and F, broussochalcones A, and B, isobavachalcone, 2,4,2',4'-tetrahydroxychalcone, moracins D, I, and M, (3S,5R)-loliolide, marmesin, trans-resveratrol, and 5,7-dihydrocoumarin were evaluated and found to be inactive as inhibitors of aromatase (IC$_{50}$ >40 mg/mL).

Results and Discussion

Compound 1 gave a molecular ion [M]$^+$ at m/z 422.1719 by HERIMS, consistent with an elemental formula of $C_{25}H_{26}O_6$. In the $^1$H NMR spectrum of compound 1 (Table 1), characteristic proton signals for a geranyl unit ($\delta_H$ 3.12 (2H, J=6.9 Hz, H-1"), $\delta_H$ 5.14 (1H, multiplet, H-2"), $\delta_H$ 1.89 (2H, multiplet, H-4"), $\delta_H$ 1.43 (3H, singlet, H-5"), $\delta_H$ 2.00 (2H, multiplet, H-6"), $\delta_H$ 5.04 (1H, multiplet, H-7"), $\delta_H$ 1.61 (3H, singlet, H-9"), and $\delta_H$ 1.55 (3H, singlet, H-10")), a set of meta-coupled proton signals ($\delta_H$ 6.25 (1H, broad singlet, H-6) and $\delta_H$ 6.33 (1H, broad singlet, H-8)), and proton signals of an ABX system ($\delta_H$ 6.57 (1H, broad singlet, H-3'), $\delta_H$ 6.51 (1H, J=8.3 Hz, H-5'), and $\delta_H$ 7.19 (1H, J=8.3 Hz, H-6')) were observed. These data suggested that compound 1 has a flavone skeleton[27] with four hydroxyl groups and one geranyl substituent, and these inferences were confirmed using the APT, COSY and HMQC NMR techniques. The positions of the substituents were deduced as occurring at C-5, C-7, C-2', and C-4' (four hydroxyls) and C-3 (geranyl) using the HMBC NMR technique (see Experimental Section). Additionally, NOE correlations between H-6' and H-1", and H-2" and H-4" confirmed the position of attachment and the E stereochemistry of the geranyl group. Thus, the structure of the new compound 1 was elucidated as 5,7,2',4'-tetrahydroxy-3-geranylflavone.

The molecular formula of compound 2 was determined as $C_{25}H_{26}O_7$ by HREIMS (m/z 438.1683). The $^1$H and $^{13}$C NMR spectra of compound 2 (Table 1) were closely comparable to those of compound 1 except that there was evidence of one less aromatic proton. Careful APT, HMQC, and HMBC NMR spectral data interpretation suggested that compound 2 has a flavonol skeleton with a geranyl group at the C-6 position.[27] The positions of two hydroxyl groups in the ring B were concluded to be at C-3' and C-4' due to observed HMBC correlations (H-2'/C-2, H-6'/C-2) and the lower field shift of the H-2' proton signal at $\delta_H$ 7.81.[22] Also, the E stereochemistry of the geranyl group was confirmed by a NOE correlation between H-2" and H-4". Therefore, the new Compound 2 was assigned as 5,7,3',4'-tetrahydroxy-6-geranylflavonol.

Compound 3 showed almost the same $^1$H and $^{13}$C NMR data (Table 1) as those of compound 2 except for the presence of a methoxyl group ($\delta_H$ 3.86 (3H, singlet); $\delta_C$ 60.2). The molecular formula, $C_{26}H_{28}O_7$ (HREIMS, m/z 452.1833), was also consistent with an additional methoxyl group in compound 3 compared with compound 2. The position of the methoxyl group was determined as C-3 from the HMBC correlation between the methoxyl signal and C-3. NOE correlations between the methoxyl signal and H-2' (H-6'), and H-2" and H-4" confirmed the position of the methoxyl group and the E stereochemistry of the geranyl group, respectively. Thus, the structure of the new compound 3 was deduced as 5,7,3',4'-tetrahydroxy-3-methoxy-6-geranylflavone.

Compound 4 was obtained as an amorphous brown powder and its molecular formula established as $C_{20}H_{22}O_3$ by HREIMS (m/z 310.1564). In its $^1$H NMR spectrum (Table 2), an ABX proton system at dH 6.83 (1H, J=8.2 Hz, H-5), $\delta_H$ 6.30 (1H, J=2.4 and 8.2 Hz, H-6), and $\delta_H$ 6.24 (1H, J=2.3 Hz, H-8) and a second ABX proton system at $\delta_H$ 7.06 (1H, J=1.8 Hz, H-2'), $\delta_H$ 6.73 (1H, J=8.1 Hz, H-5'), and $\delta_H$ 7.01 (1H, J=2.0 and 8.2 Hz, H-6'), were observed. The signals at $\delta_H$ 4.83 (1H, J=2.2 and 9.6 Hz, H-2), $\delta_H$ 1.93 (1H, multiplet, H-3), $\delta_H$ 2.04 (1H, multiplet, H-3), $\delta_H$ 2.62 (1H, multiplet, H-4), and $\delta_H$ 2.80 (1H, multiplet, H-4) were coupled to each other. Also, characteristic prenyl proton signals were observed at $\delta_H$ 3.28 (2H, J=7.3 Hz, H-1"), $\delta_H$ 5.30 (1H, multiplet, H-2"), $\delta_H$ 1.68 (3H, singlet, H-4"), and $\delta_H$ 1.71 (3H, singlet, H-5"). The results obtained from the APT and HMQC NMR spectra indicated that compound 4 has a flavan skeleton with two hydroxyl groups and one prenyl substituent.[19] The positions of these functional groups were determined unambiguously as C-7 and C-4' (two hydroxyls), and C-3' (prenyl), respectively, using the HMBC NMR technique. The absolute configuration at C-2 was confirmed as S by CD data comparison with literature values for a group of flavans.[28] Accordingly, the structure of the new compound 4 was assigned as (2S)-7,4'-dihydroxy-3'-prenylflavan.

Compound 5 was obtained as an amorphous brown powder and the $^1$H and $^{13}$C NMR data of compound 5 (Table 3) were almost superimposable to those of broussonins A (18) and B except for the absence of one methoxyl signal, consistent with the molecular formula ($C_{15}H_{16}O_3$; HREIMS, m/z 244.1098) obtained. These observations suggested that compound 5 contains a 1,3-diphenyl-substituted propane unit with three hydroxyl substituents.[18] The positions of three hydroxyl groups present were confirmed as C-2', C-4', and C-4" using the COSY and HMBC NMR techniques. Thus, the structure of the new compound 5 was assigned as 1-(2,4-dihydroxyphenyl)-3-(4-hydroxyphenyl) propane.

Compound 6 was obtained as an amorphous brown powder with the molecular formula $C_{20}H_{24}O_3$ (HREIMS m/z 312.1725) In the $^1$H NMR spectrum of compound 6 (Table 3), characteristic signals were observed for a prenyl group at $\delta_H$ 3.33 (2H, J=9.6 Hz, H-1'"), OH 5.21 (1H, multiplet, H-2'"), $\delta_H$ 1.77 (3H, singlet, H-4'"), and $\delta_H$ 1.66 (3H, singlet, H-5'"), and two sets of proton signals coupled to each other at $\delta_H$ 6.27 (1H, J=8.2 Hz, H-5') and $\delta_H$ 6.68 (overlapped, H-6'), and $\delta_H$ 6.98 (2H, J=8.4 Hz, H-211) and $\delta_H$ 6.67 (overlapped, H-3'). In the aliphatic region, the signals coupled to each other at $\delta_H$ 1.80 (2H, multiplet, H-2) and $\delta_H$ 2.52 (4H, multiplet, H-1 and H-3), suggesting the presence of a 1,3-diphenylsubstituted propane unit bearing one prenyl and three hydroxyl groups, which was substantiated using the APT, HMQC, and HMBC NMR techniques.[18] Also, the positions of the functional groups were determined unambiguously as C-2', C-4', and C-4" (three hydroxyls) and C-3' (prenyl) using 2D NMR techniques (COSY and HMBC). Thus, the structure of the new Compound 6 was elucidated as 1-(2,4-dihydroxy-3-prenylphenyl)-3-(4-hydroxyphenyl) propane.

The $^1$H NMR spectrum of compound 7 ($C_{21}H_{26}O_3$; HREIMS m/z 326.1877) showed the same profile in the upfield region as that of compound 6 except for one methoxyl signal at $\delta_H$ 3.76 (3H, singlet). However, in the downfield region, the proton signals for an ABX system at $\delta_H$ 6.35 (1H, broad doublet, H-3'), $\delta_H$ 6.31 (1H, J=2.4 and 8.1 Hz, H-5'), and $\delta_H$ 6.93 (1H, J=8.1 Hz, H-6') and for a second ABX system proton signals at $\delta_H$ 6.89 (1H, broad singlet, H-2"), $\delta_H$ 6.69 (1H, J=7.8 Hz, H-5"), and $\delta_H$ 6.91 (overlapped, H-6") were observed. Thus, the carbon skeleton of compound 7 was determined as being the same as that of compound 6. The various functional groups were placed at C-4' and C-4" (two hydroxyls), C-2' (methoxyl), and C-3" (prenyl) with the aid of the HMBC NMR technique. Accordingly, the structure of the new compound 7 was assigned as 1-(4-hydroxy-2-methoxyphenyl)-3-(4-hydroxy-3-prenylphenyl)propane.

Compound 8 was obtained as an orange powder and was shown to possess a molecular formula of $C_{30}H_{28}O_9$ by positive HRFABMS (m/z [M+Na]+, 555.1577). The $^1H$ and $^{13}C$ NMR spectra of compound 8 exhibited characteristic chalcone signals at $\delta_H$ 7.80 (1H, J=15.4 Hz, H-a), $\delta_H$ 8.22 (1H, J=15.4 Hz, H-β), $\delta_C$ 117.5 (C-α), $\delta_C$ 140.9 (C-β), and $\delta_C$ 193.4 (CO), and signals for a ferulate group at $\delta_H$ 7.34 (1H, J=1.6 Hz, H-2"), $\delta_H$ 6.85 (1H, J=8.1 Hz, H-5"), $\delta_H$ 7.12 (1H, J=1.7 and 8.2 Hz, H-6"), $\delta_H$ 7.57 (1H, J=16.0 Hz, H-7"), $\delta_H$ 6.40 (1H, J=15.9 Hz, H-8"), $\delta_H$ 3.91 (3H, singlet, OCH$^3$), $\delta_C$ 145.6 (C-7"), $\delta_C$ 115.8 (C-8"), and bc 167.3 (C-9").[29] Based on these observations and by comparison of its spectral data with those of gemichalcone C,29 compound 8 was concluded to be a regioisomer of gemichalcone C. This was confirmed using a NOESY NMR experiment. Thus, the NOE correlations between H-7' and H-10', and H-8' and H-11' clearly indicated E stereochemistry of the prenyl group. Moreover, the chemical shift differences at positions C-10' and C-11' of the E and Z isomers supported the stereochemistry proposed.[29,30] Therefore, the new compound 8 was assigned as 3'-(γ-hydroxymethyl-(E)-γ-methylallyl)-2,4,2',4'-tetrahydroxychalcone 11'-O-ferulate, and has been accorded the trivial name isogemichalcone C.

Compound 9 also was obtained as an orange powder and was deduced as having a molecular formula of $C_{29}H_{26}O_8$ by positive HRFABMS (m/z [M+Na]+, 525.1884). The $^1H$ and $^{13}C$ NMR spectra of compound 9 were almost superimposable with those of compound 8 except for the ferulate moiety of the latter compound. The presence of AA'XX'-type proton signals at $\delta_H$ 7.54 (2H, J=8.6 Hz, H-2" and H-6") and $\delta_H$ 6.87 (2H, J=8.5 Hz, H-3" and H-5"), and the absence of AMX-type proton signals and any methoxy signal indicated that compound 9 has a coumarate moiety rather than a ferulate unit as in compound 8.30 The E stereochemistry was deduced in the same manner as described for compound 8. Accordingly, the structure of the new compound 9 was determined as 3'-(γ-hydroxymethyl-(E)-γ-methylallyl)-2,4,2',4'-tetrahydroxychalcone 11'-O-coumarate.

The $^1H$ and $^{13}C$ NMR data of compound 10 were almost the same as those of moracin I[31] except for the absence of one methoxyl signal. This was consistent with the molecular formula ($C_{19}H_{18}O_4$; HREIMS, m/z 310.1208) obtained. The $^1H$ NMR data of compound 10 clearly indicated the presence of a benzofuran moiety ($\delta_H$ 6.66 (1H, singlet, H-3), $\delta_H$ 7.33 (1H, J=8.4 Hz, H-4), $\delta_H$ 6.72 (1H, J 2.2 and 8.4 Hz, H-5), and $\delta_H$ 6.87 (1H, J=2.1 Hz, H-7)), a prenyl group ($\delta_H$ 3.42 (2H, J=6.3 Hz, H-1"), $\delta_H$ 5.13 (1H, multiplet, H-2"), and $\delta_H$ 1.64 (6H, s, H-4" and H-5") and meta-coupled protons (5H 6.61 (1H, J=2.5 Hz, H-2') and $\delta_H$ 6.33 (1H, J=2.5 Hz, H-4')). Thus, the structure of the new compound 10 was proposed as demethylmoracin I, and confirmed using 2D NMR techniques.

Compound 11, aminor component, was obtained as an amorphous yellow powder and its molecular formula established as $C_{20}H_{20}O_6$ by positive HRFABMS (m/z [M+H]+, 357.1327). The $^1H$ NMR spectrum of compound 11 (Table 1) revealed an ABX system of proton signals at $\delta_H$ 6.48 (overlapped, H-3'), $\delta_H$ 6.44 (1H, J=8.4 Hz, H-5'), and $\delta_H$ 7.36 (1H, J=8.4 Hz, H-6') and a set of protons coupled to each other at $\delta_H$ 7.70 (1H, J=8.4 Hz, H-5) and $\delta_H$ 6.48 (overlapped, H-6). Additionally, three proton signals at $\delta_H$ 5.75 (1H, multiplet, H-2), $\delta_H$ 2.70 (1H, multiplet, H-3), and $\delta_H$ 3.03 (1H, multiplet, H-3), and four proton signals at $\delta_H$ 3.09 (2H, multiplet, H-1"), $\delta_H$ 4.78 (1H, double of triplet, H-2"), $\delta_H$ 1.28 (3H, singlet, H-4"), and $\delta_H$ 1.21 (3H, singlet, H-5") indicated that compound 11 is based on a flavanone skeleton with a 1-hydroxy-1-methylethyldihydrofuran group.[32] The locations of each functional group were confirmed using 2D NMR techniques as C-2' and C-4' (two hydroxyls), and [2,3-h] (dihydrofuran ring). The absolute configuration at C-2 was confirmed by a negative Cotton effect in the π→π* transition region (about 290 nm) in the CD spectrum which is characteristic for the 2S configuration of flavanones.[33] Thus, the structure of the new Compound 11 was elucidated as (2S)-2',4'-dihydroxy-2"-(1-hydroxy-1-methylethyl)-dihydrofuro[2,3-h]flavanone.

Additionally, ten active compounds of previously known structures were identified as isolicoflavonol (12),[34] (2S)-abyssinone II (13),[35] (2S)-5,7,2',4'-tetrahydroxyflavanone (14),[36] (2S)euchrenone a7 (15),[37] broussoflavonol F (16),[16] (2S)naringenin (17),[38] broussonin A (18),[18] 2,4,2',4'-tetrahydroxy-3'-prenylchalcone (9),[39] moracin N (20), and albanol A (21),[41] by spectral data interpretation and comparison with literature values. Furthermore, 21 known compounds, (2S)-2',4'-dihydroxy-7-methoxy-8-prenylflavan (22),[42] (2S)-7,4'-dihydroxyflavan,[20] (2R, 3R)-lespedezaflavanone C,[43] bavachin,[44] (2R,3R)-katuranin,[45] gancaonin P,[46] (2R,3R)-5,7,2',4'-tetrahydroxyflavanonol,[47] broussonins B,[18] E,[20] and F,[20] broussochalcones A, and B,[22] isobavachalcone,[48] 2,4,2',4'-tetrahydroxychalcone,[39] moracins D,[49] I,[31] and M,[31] and (3S,5R)loliolide,[50] marmesin,[18] trans-resveratrol,[51] and 5,7-dihydrocoumarin[52] were identified in turn by comparison with published physical and spectral data. All of these 21 known compounds were inactive in the aromatase inhibition assay at the dose levels used ($IC_{50}$>40 μg/mL).

Out of a series of forty-two compounds extracted from B. papyrifera, comprising benzofurans, biphenylpropanoids, coumarins, and various types of flavonoids (chalcones, flavans, flavanones, and flavones), representatives of the latter class of compounds showed potent aromatase inhibition activity. The $IC_{50}$ values of compounds 1 and 8–21 are summarized in Table 4. Flavanone 11 ($IC_{50}$ 0.1 pM) and flavone 12[34] ($IC_{50}$ 0.1 μM) were the most potent flavonoid inhibitors obtained, exhibiting inhibition potency that was approximately 60-fold greater than aminoglutethimide, the positive control used for this assay. The functionalized chalcone 9 ($IC_{50}$ 0.5 μM) and the flavanone 13[35] ($IC_{50}$ 0.4 μM) were approximately ten times more active than aminoglutethimide.

Interestingly, the various benzofurans (demethylmoracin I (10), moracins D,[49] 1,31 M,[31] and N (20)[40]), biphenylpropanoids (5–7, broussonins A (18),[18] B,[18] E,[20] and F[20]), flavanonols [(2R,3R)lespedezaflavanone C,[43] (2R,3R)-katuranin,[45] and (2R,3R)-5,7,2',4'-tetrahydroxyflavanonol[47]), and flavans (4, 22, and (2S)-7,4'-dihydroxyflavan[20]) tested, which are quite closely related structurally to the active compounds, did not show potent aromatase inhibition. It was noted that a carbonyl group in compounds of the chalcone, flavone, and flavanone classes is required for the exhibition of potent aromatase inhibition activity. However, the presence of a C-5 hydroxyl group among the flavanones decreased activity significantly 14,[36] $IC_{50}$ 2.2 μM and 17,[38] $IC_{50}$ 17.0 μM), and flavones or flavanones with a prenyl or geranyl unit at C-6 (2, 3, bavachin,[44] and gancaonin P[46]) were not active. Presumably such a bulky substituent at C-6 prevents these compounds from interacting with the enzyme.

It has been reported that some flavonoids (flavones, flavanones, and isoflavones) inhibit aromatase activity.[25,26,53,54] In the present study, inhibition was achieved at physiologically relevant concentrations (100–1000 nM) of dietary flavonoids. Accordingly, these compounds can be useful as cancer chemopreventive agents. For example, compound 11, $IC_{50}$ 0.1 μM and compound 12,[34] $IC_{50}$ 0.1 μM) are the most potent aromatase inhibitors derived from a natural source known to date.

REFERENCES (1) Vogel, C. L., Semin. Oncol., 1996, 23 (Suppl. 9), 2–9.
(2) Reddy, P., J. Clin. Pharmacol. Ther., 1998, 23, 81–90.
(3) Henderson, D.; Habenicht, U. -F.; Nishino, Y.; el Etreby, M. F., Steroids 1987, 50, 219–233.
(4) Karr, J. P.; Kaburagi, Y.; Mann, C. F.; Sandberg, A. A., Steroids, 1987, 50, 441–449.
(5) Kelloff, G. J.; Lubet, R. A.; Lieberman, R.; Eisenhauer, K.; Steele, V. E.; Crowell, J. A.; Hawk, E. T.; Boone, C. W.; Sigman, C. C., Cancer Epidemiol. Biomark. Prev., 1998, 7, 65–78.
(6) Siiteri, P. K., Cancer Res., 1982, 42 (Suppl. 8), 3269s–3273s.
(7) Brodie, A. M. H.; Njar, V. C. O., Semin. Oncol., 1996, 23 (Suppl. 9), 10–20.
(8) Chiang Su New Medicinal College, Ed. Dictionary of Chinese Crude Drugs; Shanghai Scientific Technologic Publisher: Shanghai, 1986; pp 2289–2290.
(9) Matsuda, H.; Cai, H.; Kubo, M.; Tosa, H.; Iinuma, M., Biol. Pharm. Bull., 1995, 18, 463–466.
(10) Kim, S. Y.; Kim, J. H.; Kim, S. K.; Oh, M. J.; Jung, M. Y., J. Am. Oil Chem. Soc., 1994, 71, 633–640.
(11) Kim, Y. S.; Park, K. H., Kor. J. Pharmacogn., 1994, 25, 388–394.
(12) Shirata, A.; Takahashi, K., Sanshi Shikenjo Hokoku, 1982, 28, 691–705.
(13) Ko, H. -H.; Yu, S. -M.; Ko, F. -N.; Teng, C. -M.; Lin, C. -N., J. Nat. Prod., 1997, 60, 1008–1011.
(14) Lin, C. -N.; Lu, C. -M.; Lin, H. -C.; Fang, S. -C.; Shieh, B. -J.; Hsu, M. -F.; Wang, J. -P.; Ko, F. -N.; Teng, C. -M., J. Nat. Prod., 1996, 59, 834–838.
(15) Fang, S. -C.; Shieh, B. -J.; Lin, C. -N., Phytochemistry, 1994, 37, 851–853.
(16) Liang, P. W.; Chen, C. C.; Chen, Y. P.; Hsu, H. Y., Hua Hsueh Hsueh Pao, 1986, 44, 152–154.
(17) Fang, S. -C.; Shieh, B. -J.; Wu, R. -R.; Lin, C. -N., Phytochemistry, 1995, 38, 535–537.
(18) Takasugi, M.; Anetai, M.; Masamune, T.; Shirata, A.; Takahashi, K., Chem. Lett., 1980, 339–340.
(19) Takasugi, M.; Kumagai, Y.; Nagao, S.; Masamune, T.; Shirata, A.; Takahashi, K., Chem. Lett., 1980, 1459–1460.
(20) Takasugi, M.; Niino, N.; Nagao, S.; Anetai, M.; Masamune, T.; Shirata, A.; Takahashi, K., Chem. Lett., 1984, 689–692.
(21) Takasugi, M.; Niino, N.; Anetai, M.; Masamune, T.; Shirata, A.; Takahashi, K., Chem. Lett., 1984, 693–694.
(22) Matsumoto, J.; Fujimoto, T.; Takino, C.; Saitoh, M.; Hano, Y.; Fukai, T.; Nomura, T., Chem. Pharm. Bull., 1985, 33, 3250–3256.
(23) Ikuta, J.; Hano, Y.; Nomura, T., Heterocycles, 1985, 23, 2835–2842.
(24) Fukai, T.; Ikuta, J.; Nomura, T., Chem. Pharm. Bull., 1986, 34, 1987–1993.
(25) Jeong, H. -J.; Shin, Y. G.; Kim, I. -H.; Pezzuto, J. M., Arch. Pharmacal Res., 1999, 22, 309–312.
(26) Le Bail, J. C.; Laroche, T.; Marre-Fournier, F.; Habrioux, G., Cancer Lett., 1998, 133, 101–106.
(27) Ferrari, F.; Messana, I.; Mesquita de Araujo, M. C., Planta Med., 1989, 55, 70–72.
(28) Cardillo, G.; Merlini, L.; Nasini, G., J. Chem. Soc. (C), 1971, 3967–3970.
(29) Chung, M. -I.; Weng, J. -R.; Lai, M.—H.; Yen, M. -H.; Lin, C. -N., J. Nat. Prod., 1999, 62, 1033–1035.
(30) Chung, M. -I.; Lai, M. -H.; Yen, M. -H.; Wu, R. -R.; Lin, C. -N., Phytochemistry, 1997, 44, 943–947.
(31) Mann, I. S.; Widdowson, D. A.; Clough, J. M., Tetrahedron, 1991, 47, 7991–8000.
(32) Roussis, V.; Ampofo, S. A.; Wiemer, D. F., Phytochemistry, 1987, 26, 2371–2375.
(33) Gaffield, W., Tetrahedron, 1970, 26, 4093–4108.
(34) Hanato, T.; Kagawa, H.; Yasuhara, T.; Okuda, T., Chem. Pharm. Bull., 1988, 36, 2090–2097.
(35) Kamat, V. S.; Chou, F. Y.; Kubo, I.; Nakanishi, K., Heterocycles, 1981, 15, 1163–1170.
(36) Chang, C. -H.; Lin, C. -C.; Kadota, S.; Hattori, M.; Namba, T., Phytochemistry, 1995, 40, 945–947.
(37) Mizuno, M.; Tanaka, T.; Matsuura, N.; Iinuma, M.; Cheih, C., Phytochemistry, 1990, 29, 2738–2740.
(38) Barros, D. A. D.; de Alvarenga, M. A.; Gottlieb, O. R.; Gottlieb, H. E., Phytochemistry, 1982, 21, 2107–2109.
(39) delle Monache, G.; de Rosa, M. C.; Scurria, R.; Vitali, A.; Cuteri, A.; Monacelli, B.; Pasqua, G.; Botta, B. Phytochemistry, 1995, 39, 575–580.
(40) Matsuyama, S.; Kuwahara, Y.; Nakamura, S.; Suzuki, T., Agric. Biol. Chem., 1991, 55, 1333–1341.
(41) Rama Rao, A. V.; Deshpande, V. H.; Shastri, R. K.; Ravale, S. S.; Dhaneshwar, N. N., Tetrahedron Lett., 1983, 24, 3013–3016.
(42) Doi K. et al., Chem. Pharm. Bull., 2001, 49, 151–153.
(43) Li, J.; Wang, M., Phytochemistry, 1989, 28, 3564–3566.
(44) Bhalla, V. K.; Nayak, U. R.; Dev, S., Tetrahedron Lett., 1968, 20, 2401–2406.
(45) Reisch, J.; Hussain, R. A.; Mester, I., Phytochemistry, 1984, 23, 2114–2115.
(46) Fukai, T.; Wang, Q. -H.; Takayama, M.; Nomura, T., Heterocycles, 1990, 31, 373–382.
(47) Gerber, N. N., Phytochemistry, 1986, 25, 1697–1699.
(48) Pistelli, L.; Spera, K.; Flamini, G.; Mele, S.; Morelli, I., Phytochemistry, 1996, 42, 1455–1458.
(49) Takasugi, M.; Nagao, S.; Ueno, S.; Masamune, T.; Shirata, A.; Takahashi, K., Chem. Lett., 1978, 1239–1240.
(50) Fernandez, I.; Pedro, J. R.; Vidal, R., Phytochemistry, 1993, 34, 733–736.
(51) Mannila, E.; Talvitie, A.; Kolehmainen, E., Phytochemistry, 1993, 33, 813–816.
(52) Hirakura, K.; Saida, I.; Fukai, T.; Nomura, T., Heterocycles, 1985, 23, 2239–2242.
(53) Kellis, J. T.; Vickery, L. E., Science, 1984, 225, 1032–1034.
(54) Ibrahim, A. -R.; Abul-Hajj, Y. J., J. Steroid Biochem. Molec. Biol., 1990, 37, 257–260.
(55) Thompson, E. A.; Siiteri, P. K., J. Biol. Chem., 1974, 249, 5373–5378.
(56) Rabe, T.; Rabe, D.; Punnebaum, B., J. Steroid Biochem., 1982, 7, 305–309.

Modifications and variations of the invention as hereinbefore set forth can be made without departing from the spirit and scope thereof, and, therefore, only such limitations should be imposed as are indicated by the appended claims.

What is claimed is:

1. A composition comprising (a) about 0.1% to about 75%, by weight, of a compound selected from the group consisting of 5,7,2',4'-tetrahydroxy-3-geranylflavone, isogemichalcone C, 3'-(γ-hydroxymethyl-(E)-γ-methylallyl)-2,4,2',4'-tetrahydroxychalcone 11'-O-coumarate, demethylmoracin I, 2S-2',4'-dihydroxy-2"-(1-hydroxy-1-methylethyl) -dihydrofuro[2,3-h]flavanone, (2S)-2',4'-di-hydroxy-7-methoxy-8-prenylflavan, isolicoflavonol, (2S)-abyssinone II, (2S)-5,7,2',4'-tetrahydroxyflavanone, (2S)-euchrenone a7, broussoflavonol F, (2S)-naringenin, broussonin A, 2,4,2',4'-tetrahydroxy-3'-prenylchalcone, moracin N, albanol A, and mixtures thereof, and (b) an excipient.

2. The composition of claim 1 comprising a compound selected from the group consisting of 3'-(-hydroxymethyl-(E)-γ-methylallyl)2,4,2',4'-tetrahydroxychalcone 11'-O-coumarate, 2S-abyssinone II, (2S)-2',4'-dihydroxy-2"-(1-hydroxy-l-methylethyl)-dihydrofuro [2,3-h]flavanone, isolicoflavonol, and mixtures thereof.

3. The composition of claim 1 comprising a compound selected from the group consisting of isolicoflavonol, 2S-abyssinone II, and (2S)-2',4'-dihydroxy-2"-(l-hydroxy-1-methylethyl)-dihydrofuro [2,3-h]flavanone, and mixtures thereof.

4. The composition of claim 1 wherein the compound has an $IC_{50}$ value versus aromatase of about 35 μM or less.

5. The composition of claim 1 wherein the compound has an $IC_{50}$ value versus aromatase of about 20 μM or less.

6. A composition consisting essentially of (a) about 0.1% to about 75%, by weight, of a compound selected from the group consisting of 5,7,2',4'-tetrahydroxy-3-geranyiflavone, isogemichalcone C, 3'-(γ-hydroxymethyl-(E)-γ-methylallyl)-2,4,2',4'-tetrahydroxychalcone 11'-O-coumarate, demethylmoracin I, 2S-2',4'-dihydroxy-2"-(l-hydroxy-l-methyl-ethyl)-dihydrofuro[2,3-h]flavanone, (2S)-2',4'-dihydroxy-7-methoxy-8-prenylflavan, isolicoflavonol, (2S)-abyssinone II, (2S)-5,7,2',4'-tetrahydroxyflavanone, (2S)-euchrenone a7, broussoflavonol F, (2S)-naringenin, broussonin A, 2,4,2',4'-tetrahydroxy-3'-prenylchalcone, moracin N, albanol A, and mixtures thereof, and (b) an excipient.

7. A method of treating a medical condition characterized by estrogen biosynthesis and mediated by aromatase activity comprising administering to an animal in need thereof a therapeutically effective amount of a compound selected from the group consisting of 5,7,2',4'-tetrahydroxy-3-geranylflavone, isogemichalcone C, 3'-(γ-methylallyl)2,4,2',4'-tetrahydroxy-chalcone 11'-O-coumarate, demethylmoracin I, 2S-2',4'-dihydroxy-2'-(1-hydroxy-l-methylethyl)-dihydrofuro[2,3-h]flavanone, (2S)-2',4'-dihydroxy-7-methoxy-8-prenylflavan, isolicoflavonol, (2S)-abyssinone II, (2S)-5,7,2',4'-tetrahydroxyflavanone, (2S)-euchrenone a7, broussoflavonol F, (2S)-naringenin, broussonin A, 2,4, 2',4'-tetrahydroxy-3'-prenylchalcone, moracin N, albanol A, and mixtures thereof.

8. The method of claim 7 where in the compound selectively inhibits aromatase activity relative to related enzyme family members.

9. The method of claim 7 wherein production of steroid production other than estrogen is substantially unaffected.

10. A method of inhibiting the biosynthetic production of estrogen in a mammal comprising administering to the mammal a therapeutically effective amount of a compound selected from the group consisting of 5,7,2',4'-tetrahydroxy-3-geranylflavone, isogemichalcone C, 3'-(γ-methylallyl)-2, 4,2',4'-tetrahydroxychalcone 11'-O-coumarate, demethylmoracin I, 2S-2',4'-dihydroxy-2'-(l-hydroxy-1-methylethyl)-dihydrofuro[2,3-h]flavanone, (2S)-2', 4'-dihydroxy-7-methoxy-8-prenylflavan, isolicoflavonol, (2S)-abyssinone II, (2S)-5,7,2',4'-tetrahydroxyflavanone, (2S)-euchrenone a7, broussoflavonol F, (2S)-naringenin, broussonin A, 2,4, 2',4'-tetrahydroxy-3'-prenylchalcone, moracin N, albanol A, and mixtures thereof.

11. A method of treating a breast cancer or a prostate cancer comprising administering a pharmaceutical composition to a mammal in need thereof in a sufficient amount to suppress the initiation, promotion, or progression of the breast or prostate cancer, said composition comprising: (a) a compound selected from the group consisting of 5,7,2',4'-tetrahydroxy-3-geranylflavone, isogemichalcone C, 3'-(γ-hydroxymethyl-(E)-γ-methylallyl) 2,4,2',4'-tetrahydroxychalcone 11'-O-coumarate, demethylmoracin I, 2S-2',4'-dihydroxy-2"-(1-hydroxy-1-methylethyl)-dihydrofuro[2,3-h]flavanone, (2S)-2',4'-dihydroxy-7-methoxy-8-prenylflavan, isolicoflavonol, (2S)-abyssinone II, (2S)-5,7,2',4'-tetrahydroxyflavanone, (2S)-euchrenone a7, broussoflavonol F, (2S)-naringenin, broussonin A, 2,4, 2',4'-tetrahydroxy-3'-prenylchalcone, moracin N, albanol A, and mixtures thereof, and (b) an excipient.

12. The method of claim 11 wherein the composition is a solid.

13. The method of claim 11 wherein the composition is a liquid.

14. The method of claim 11 wherein the composition is administered orally.

15. The method of claim 11 wherein the composition is administered parenterally.

16. The method of claim 11 wherein the mammal is a human.

17. A compound selected from the group consisting of 5,7,2',4'-tetrahydroxy-3-geranylflavone, isogemichalcone C, 3'-(γ-hydroxymethyl-(E)-γ-methylallyl)-2,4,2',4'-tetrahydroxychalcone 11'-O-coumarate, demethylmoracin I, and (2S)-2',4'-dihydroxy-2"-(1-hydroxy-1-methylethyl)-dihydrofuro[2, 3-h]flavanone, 5,7,3',4'-tetrahydroxy-6-geranylflavonol, 5,7,3',4'-tetrahydroxy-3-methoxy-6-geranylflavone, (2S)-7,4'-dihydroxy-3'-prenylflavan, 1-(2,4-dihydroxyphenyl)-3-(4-hydroxyphenyl)propane, 1-(2,4-dihydroxy-3-prenylphenyl)-3-(4-hydroxyphenyl)propane, and 1-(4-hydroxy-2-methoxyphenyl)-3-(4-hydroxy-3-prenylphenyl)-propane.

18. The compound of claim 17 selected from the group consisting of 5,7,2',4'-tetrahydroxy-3-geranylflavone, isogemichalcone C, 3'-(γ-hydroxymethyl-(E)-γ-methylallyl)-2,4,2',4'-tetrahydroxychalcone 11'-O-coumarate (9), demethylmoracin I, and (2S)-2',4'-dihydroxy-2"-(l-hydroxy-1-methylethyl)-dihydrofuro[2,3-h]flavanone.

* * * * *

UNITED STATES PATENT AND TRADEMARK OFFICE
CERTIFICATE OF CORRECTION

PATENT NO. : 6,737,439 B2
DATED : May 18, 2004
INVENTOR(S) : Alan Douglas Kinghorn et al.

It is certified that error appears in the above-identified patent and that said Letters Patent is hereby corrected as shown below:

Title page,
Item [57], ABSTRACT,
Line 2, "utilized" should be -- utilize --

Column 33,
Line 32, "-geranyiflavone" should be -- geranylflavone --
Line 36, "-methyl-ethyl" should be -- methylethyl --
Line 50, "dihydroxy-2'-" should be -- dihydroxy-2"- --
Line 57, "where in" should be -- wherein --

Column 34,
Line 7, "dihydroxy-2'-" should be -- dihydroxy-2"- --

Signed and Sealed this

Second Day of November, 2004

JON W. DUDAS
*Director of the United States Patent and Trademark Office*